United States Patent
Weber et al.

(12)

(10) Patent No.: US 6,582,701 B1
(45) Date of Patent: Jun. 24, 2003

(54) EQUINE FC EPSILON RECEPTOR ALPHA CHAIN PROTEINS AND USES THEREOF

(75) Inventors: Eric R. Weber, Fort Collins, CO (US); Catherine A. McCall, Boulder, CO (US)

(73) Assignee: Heska Corporation, Fort Collins, CO (US)

(*) Notice: Subject to any disclaimer, the term of this patent is extended or adjusted under 35 U.S.C. 154(b) by 0 days.

(21) Appl. No.: 09/515,311

(22) Filed: Feb. 29, 2000

Related U.S. Application Data

(62) Division of application No. 09/015,734, filed on Jan. 29, 1998, now Pat. No. 6,057,127.

(51) Int. Cl.$^7$ .................. A61K 39/00; C07K 14/705
(52) U.S. Cl. .................. 424/185.1; 530/350
(58) Field of Search .................. 530/350; 424/185.1

(56) References Cited

U.S. PATENT DOCUMENTS 4,962,035 A    10/1990    Leder et al.

FOREIGN PATENT DOCUMENTS

| JP | 51113443 | 5/1993 |
| WO | WO 89/05352 A | 6/1989 |
| WO | WO 90/04640 | 5/1990 |
| WO | WO 91/06570 | 5/1991 |
| WO | WO 93/04173 A | 3/1993 |

OTHER PUBLICATIONS

Hayashi, et al., Genbank Accession No. D16413, submitted Jun. 8, 1993.
Kochan, et al., "Isolation of the Gene Coding for the Alpha Subunit of the Human High Affinity IgE Receptor," (1988) *Nucleic Acids Res.* 16(8), p. 3584.
Küster, et al., "Characterization and Expression of the Gene for the Human Fc Receptor γSubunit," (1990) *J. Biol. Chem.* 265(11), pp. 6448–6452.
Küster, et al., "The Gene and cDNA for the Human High Affinity Immunoglobulin E Receptor βChain and Expression of the Complete Human Receptor," (1992) *J. Biol. Chem.* 267(18), pp. 12782–12787.

Lowenthal, et al., "Passive Transfer of IgE–Mediated Cutaneous Reactivity in Heterologous Species," (1993) *Annals of Allergy* 71, pp. 481–484.
Pang, et al., "Characterization of the Gene for the Human High Affinity IgE Receptor (FcεRI) α–Chain," (1993) *J. Immunol.* 151(11), pp. 6166–6174.
Ra, et al., "Complete Structure of the Mouse Mast Cell Receptor for IgE (FcεRI) and Surface Expression of Chimeric Receptors (Rat–Mouse–Human) on Transfected Cells," (1989) *Journal of Biological Chemistry* vol. 264(26), pp. 15323–15327.
Ravetch, et al., "Fc Receptors," (1991), *Annu. Rev. Immunol.* (9), pp. 457–492.
Shimizu, et al., "Human and Rat Mast Cell High–Affinity Immunoglobulin E Receptors: Characterization of Putative α–Chain Gene Products," (1988), *Proc. Natl. Acad. Sci. USA* (85), pp. 1907–1911.
Mikayama et al. (PNAS, 1993. 90: 10056–10060).*
Skolnick and Fetrow (Trends in Biotechnology, 2000. 18(1): 34–39).*
Ngo et al, in The Protein Folding Problem and Tertiary Structure Prediction, 1994. (ed.), Birkhauser, Boston, MA, pp. 433 and 492–495.*
Current Protocols in Molecular Biology (Chapter 2, Section IV, Unit 2.10 from John Wiley & Sons, Inc., 2002, the Introduction and the Commentary).*
Ngo et al . The Protein Folding Problem and Tertiary Structure Prediction. K. Merz Jr. and S. Le Grand, Editors, Birhuaser Boston, 1994, pp. 194–495.*
Chatterjee et al. Canc. Immunol. Immunother. 38: 75–82, 1994.*

* cited by examiner

*Primary Examiner*—Christina Chan
*Assistant Examiner*—Phuong N. Huynh
(74) *Attorney, Agent, or Firm*—Heska Corporation

(57) ABSTRACT

The present invention relates to equine Fc epsilon receptor alpha chain nucleic acid molecules, proteins encoded by such nucleic acid molecules, antibodies raised against such proteins, and inhibitors of such proteins. The present invention also includes methods to detect IgE using such proteins and antibodies. Also included in the present invention are therapeutic compositions comprising such proteins, nucleic acid molecules, antibodies and/or inhibitory compounds as well as the use of such therapeutic compositions to mediate Fc epsilon receptor-mediated biological responses.

8 Claims, No Drawings

EQUINE FC EPSILON RECEPTOR ALPHA CHAIN PROTEINS AND USES THEREOF

This Application is a Divisional Application of application Ser. No. 09/015,734, filed Jan. 29, 1998, now U.S. Pat. No. 6,057,127 entitled "NOVEL EQUINE Fc EPSILON RECEPTOR ALPHA CHAIN NUCLEIC ACID MOLECULES, PROTEINS AND USES THEREOF", which is incorporated herein by this reference in its entirety.

FIELD OF THE INVENTION

The present invention relates to equine Fc epsilon receptor alpha chain nucleic acid molecules, proteins encoded by such nucleic acid molecules, antibodies raised against such proteins, and inhibitors of such proteins. The present invention also includes methods to detect IgE using such proteins and antibodies.

BACKGROUND OF THE INVENTION

Diagnosis of disease and determination of treatment efficacy are important tools in medicine. IgE antibody production in an animal can be indicative of disease including, for example, allergy, atopic disease, hyper IgE syndrome, internal parasite infections and B cell neoplasia. In addition, detection of IgE production in an animal following a treatment is indicative of the efficacy of the treatment, such as when using treatments intended to disrupt IgE production.

Immunological stimulation can be mediated by IgE antibodies when IgE complexes with Fc epsilon receptors. Fc epsilon receptors are found on the surface of certain cell types, such as mast cells. Mast cells store biological mediators including histamine, prostaglandins and proteases. Release of these biological mediators is triggered when IgE antibodies complex with Fc epsilon receptors on the surface of a cell. Clinical symptoms result from the release of the biological mediators into the tissue of an animal.

The discovery of the present invention includes a novel equine Fc epsilon receptor ($Fc_\epsilon R$) alpha chain protein and the use of such a protein to detect the presence of IgE in a putative IgE-containing composition; to identify inhibitors of biological responses mediated by an equine $Fc_\epsilon R$ protein; and as a therapeutic compound to prevent or treat clinical symptoms that result from equine $Fc_\epsilon R$-mediated biological responses.

Prior investigators have disclosed the nucleic acid sequence for: the human $Fc_\epsilon R$ alpha chain (Kochan et al., *Nucleic Acids Res.* 16:3584, 1988; Shimizu et al., *Proc. Natl. Acad. Sci. USA* 85:1907–1911, 1988; and Pang et al., *J. Immunol.* 151:6166–6174, 1993); the human $Fc_\epsilon R$ beta chain (Kuster et al., *J. Biol. Chem.* 267:12782–12787, 1992); the human $Fc_\epsilon R$ gamma chain (Kuster et al., *J. Biol. Chem.* 265:6448–6452, 1990); and the canine $Fc_\epsilon R$ alpha chain (GenBank™ accession number D16413). Although the subunits of human $Fc_\epsilon R$ have been known as early as 1988, they have never been used to identify an equine $Fc_\epsilon R$. Similarly, even though the canine $Fc_\epsilon R$ chain has been known since 1993, it has never been used to identify an equine $Fc_\epsilon R$. Moreover, the determination of human and canine Fc epsilon receptor sequences does not indicate, suggest or predict the cloning of a novel $Fc_\epsilon R$ gene from a different species, in particular, from an equine species. Previous investigators have found a low degree of similarity between rat, mouse and human $Fc_\epsilon R\alpha$ (Ravtech et al., Ann. Rev. Immunol. Vol. 9, pp. 457–492, 1991). Thus, given this low degree of sequence similarity, it would appear only "obvious to try" to obtain an equine $Fc_\epsilon R\alpha$ nucleic acid molecule and protein.

Thus, products and processes of the present invention are needed in the art that will provide specific detection of IgE, in particular equine IgE, and treatment of Fc epsilon receptor-mediated disease.

SUMMARY OF THE INVENTION

The present invention relates to a novel product and process for detecting IgE and protecting animals from Fc epsilon receptor-mediated biological responses. According to the present invention there are provided equine $Fc_\epsilon R$ proteins and mimetopes thereof; equine $Fc_\epsilon R$ nucleic acid molecules, including those that encode such proteins; antibodies raised against such equine $Fc_\epsilon R$ proteins (i.e., anti-equine $Fc_\epsilon R$ antibodies); and other compounds that inhibit the ability of equine $Fc_\epsilon R$ protein to form a complex with IgE (i.e, inhibitory compounds or inhibitors).

The present invention also includes methods to obtain such proteins, mimetopes, nucleic acid molecules, antibodies and inhibitory compounds. Also included in the present invention are therapeutic compositions comprising such proteins, mimetopes, nucleic acid molecules, antibodies, and/or inhibitory compounds, as well as use of such therapeutic compositions to Fc epsilon receptor-mediated biological responses.

One embodiment of the present invention is an isolated nucleic acid molecule encoding an equine $Fc_\epsilon R$ protein. The equine $Fc_\epsilon R$ protein preferably includes: proteins comprising amino acid sequences SEQ ID NO:2, SEQ ID NO:7 and SEQ ID NO:12; and proteins encoded by allelic variants of nucleic acid molecules encoding a protein comprising any of the amino acid sequences. Particularly preferred equine $Fc_\epsilon R$ nucleic acid molecules include: nucleic acid molecules comprising nucleic acid sequences SEQ ID NO:1, SEQ ID NO:3, SEQ ID NO:4, SEQ ID NO:5, SEQ ID NO:6, SEQ ID NO:8 and SEQ ID NO:11 and nucleic acid molecules comprising allelic variants of nucleic acid molecules comprising nucleic acid sequences SEQ ID NO:1, SEQ ID NO:3, SEQ ID NO:4, SEQ ID NO:5, SEQ ID NO:6, SEQ ID NO:8 and SEQ ID NO:11.

The present invention also includes an isolated equine $Fc_\epsilon R$ protein. A preferred equine $Fc_\epsilon R$ protein is encoded by a nucleic acid molecule that hybridizes under stringent hybridization conditions to a nucleic acid sequence including SEQ ID NO:3, SEQ ID NO:5 and SEQ ID NO:8. Particularly preferred equine $Fc_\epsilon R$ proteins include at least one of the following amino acid sequences: SEQ ID NO:2, SEQ ID NO:7 and SEQ ID NO:12.

The present invention also relates to recombinant molecules, recombinant viruses and recombinant cells that include equine $Fc_\epsilon R$ nucleic acid molecules of the present invention. Also included are methods to produce such nucleic acid molecules, recombinant molecules, recombinant viruses and recombinant cells.

The present invention also includes detection methods and kits that detect IgE. One embodiment of the present invention is a method to detect IgE comprising: (a) contacting an isolated equine $Fc_\epsilon R$ molecule with a putative IgE-containing composition under conditions suitable for formation of a $Fc_\epsilon R$ molecule:IgE complex; and (b) determining the presence of IgE by detecting the $Fc_\epsilon R$ molecule:IgE complex, the presence of the $FC_\epsilon R$ molecule:IgE complex indicating the presence of IgE. A preferred equine $Fc_\epsilon R$ molecule is one in which a carbohydrate group of the equine $Fc_\epsilon R$ molecule is conjugated to biotin.

Another embodiment of the present invention is a method to detect IgE comprising: (a) contacting a recombinant cell with a putative IgE-containing composition under conditions suitable for formation of a recombinant cell:IgE complex, in which the recombinant cell comprises an equine Fc$_\epsilon$R molecule; and (b) determining the presence of IgE by detecting the recombinant cell:IgE complex, the presence of the recombinant cell:IgE complex indicating the presence of IgE. A preferred method to detect IgE comprises: (a) immobilizing the Fc$_\epsilon$R molecule on a substrate; (b) contacting the Fc$_\epsilon$R molecule with the putative IgE-containing composition under conditions suitable for formation of a Fc$_\epsilon$R molecule:IgE complex bound to the substrate; (c) removing non-bound material from the substrate under conditions that retain Fc$_\epsilon$R molecule:IgE complex binding to the substrate; and (d) detecting the presence of the Fc$_\epsilon$R molecule:IgE complex. Another preferred method to detect IgE comprises: (a) immobilizing a specific antigen on a substrate; (b) contacting the antigen with the putative IgE-containing composition under conditions suitable for formation of an antigen:IgE complex bound to the substrate; (c) removing non-bound material from the substrate under conditions that retain antigen:IgE complex binding to said substrate; and (d) detecting the presence of the antigen:IgE complex by contacting the antigen:IgE complex with said Fc$_\epsilon$R molecule. Another preferred method to detect IgE comprises: (a) immobilizing an antibody that binds selectively to IgE on a substrate; (b) contacting the antibody with the putative IgE-containing composition under conditions suitable for formation of an antibody:IgE complex bound to the substrate; (c) removing non-bound material from the substrate under conditions that retain antibody:IgE complex binding to the substrate; and (d) detecting the presence of the antibody:IgE complex by contacting the antibody:IgE complex with said Fc$_\epsilon$R molecule. Another preferred method to detect IgE comprises: (a) immobilizing a putative IgE-containing composition on a substrate; (b) contacting the composition with the Fc$_\epsilon$R molecule under conditions suitable for formation of a Fc$_\epsilon$R molecule:IgE complex bound to the substrate; (c) removing non-bound material from the substrate under conditions that retain Fc$_\epsilon$R molecule:IgE complex binding to the substrate; and (d) detecting the presence of the Fc$_\epsilon$R molecule:IgE complex.

The present invention also includes a kit for performing methods of the present invention. One embodiment is a kit for detecting IgE comprising an equine Fc$_\epsilon$R protein and a means for detecting IgE.

The present invention also includes an inhibitor that interferes with formation of a complex between equine Fc$_\epsilon$R protein and IgE, in which the inhibitor is identified by its ability to interfere with the complex formation. A particularly preferred inhibitor includes a substrate analog of an equine Fc$_\epsilon$R protein, a mimetope of an equine Fc$_\epsilon$R protein and a soluble portion of an equine Fc$_\epsilon$R protein. Also included is a method to identify a compound that interferes with formation of a complex between equine Fc$_\epsilon$R protein and IgE, the method comprising: (a) contacting an isolated equine Fc$_\epsilon$R protein with a putative inhibitory compound under conditions in which, in the absence of the compound, the equine Fc$_\epsilon$R protein forms a complex with IgE; and (b) determining if the putative inhibitory compound inhibits the complex formation. A test kit is also included to identify a compound capable of interfering with formation of a complex between an equine Fc$_\epsilon$R protein and IgE, the test kit comprising an isolated equine Fc$_\epsilon$R protein that can complex with IgE and a means for determining the extent of interference of the complex formation in the presence of a putative inhibitory compound.

Yet another embodiment of the present invention is a therapeutic composition that is capable of reducing Fc epsilon receptor-mediated biological responses. Such a therapeutic composition includes one or more of the following therapeutic compounds: an isolated equine Fc$_\epsilon$R protein; a mimetope of an equine Fc$_\epsilon$R protein; an isolated nucleic acid molecule that hybridizes under stringent hybridization conditions with an equine Fc$_\epsilon$R gene; an isolated antibody that selectively binds to an equine Fc$_\epsilon$R protein; and an inhibitor that interferes with formation of a complex between an equine Fc$_\epsilon$R protein and IgE. A method of the present invention includes the step of administering to an animal a therapeutic composition of the present invention.

Yet another embodiment of the present invention is a method to produce an equine Fc$_\epsilon$R protein, the method comprising culturing a cell transformed with a nucleic acid molecule encoding an equine Fc$_\epsilon$R protein.

DETAILED DESCRIPTION OF THE INVENTION

The present invention provides for isolated equine Fc epsilon receptor alpha chain (Fc$_\epsilon$R$\alpha$) proteins, isolated equine Fc$_\epsilon$R$\alpha$ nucleic acid molecules, antibodies directed against equine Fc$_\epsilon$R$\alpha$ proteins and other inhibitors of equine Fc$_\epsilon$R$\alpha$ activity. As used herein, the terms isolated equine Fc$_\epsilon$R$\alpha$ proteins and isolated equine Fc$_\epsilon$R$\alpha$ nucleic acid molecules refers to Fc$_\epsilon$R$\alpha$ proteins and Fc$_\epsilon$R$\alpha$ nucleic acid molecules derived from horses and, as such, can be obtained from their natural source or can be produced using, for example, recombinant nucleic acid technology or chemical synthesis. Also included in the present invention is the use of these proteins and antibodies in a method to detect epsilon immunoglobulin (referred to herein as IgE or IgE antibody) as well as in other applications, such as those disclosed below. The products and processes of the present invention are advantageous because they enable the detection of IgE and the inhibition of IgE or equine Fc$_\epsilon$R$\alpha$ protein activity associated with disease. As used herein, equine Fc epsilon alpha chain receptor protein can be referred to as Fc$_\epsilon$R$\alpha$ protein or Fc$_\epsilon$R alpha chain protein.

One embodiment of the present invention is an isolated protein comprising an equine Fc$_\epsilon$R$\alpha$ protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis.

As used herein, an isolated equine Fc$_\epsilon$R$\alpha$ protein can be a full length protein or any homolog of such a protein. As used herein, a protein can be a polypeptide or a peptide. Preferably, an equine Fc$_\epsilon$R$\alpha$ protein comprises at least a portion of an equine Fc$_\epsilon$R$\alpha$ protein that binds to IgE, i.e., that is capable of forming a complex with an IgE.

An equine Fc$_\epsilon$R$\alpha$ protein of the present invention, including a homolog, can be identified in a straight-forward manner by the protein's ability to bind to IgE. Examples of equine Fc$_\epsilon$R$\alpha$ protein homologs include equine Fc$_\epsilon$R$\alpha$ proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog is capable of binding to IgE.

Equine Fc$_\epsilon$R$\alpha$ protein homologs can be the result of natural allelic variation or natural mutation. Equine Fc$_\epsilon$R$\alpha$ protein homologs of the present invention can also be produced using techniques known in the art including, but not limited to, direct modifications to the protein or modifications to the gene encoding the protein using, for example, classic or recombinant nucleic acid techniques to effect random or targeted mutagenesis.

Isolated equine Fc$_\epsilon$R$\alpha$ proteins of the present invention have the further characteristic of being encoded by nucleic acid molecules that hybridize under stringent hybridization conditions to a gene encoding an equine Fc$_\epsilon$R$\alpha$ protein. As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

As used herein, an equine Fc$_\epsilon$R$\alpha$ gene includes all nucleic acid sequences related to a natural equine Fc$_\epsilon$R$\alpha$ gene such as regulatory regions that control production of the equine Fc$_\epsilon$R$\alpha$ protein encoded by that gene (such as, but not limited to, transcription, translation or post-translation control regions) as well as the coding region itself. In one embodiment, an equine Fc$_\epsilon$R$\alpha$ gene of the present invention includes nucleic acid sequence SEQ ID NO:1, SEQ ID NO:3, SEQ ID NO:4, SEQ ID NO:5, SEQ ID NO:6, SEQ ID NO:8 and/or SEQ ID NO:11. Nucleic acid sequence SEQ ID NO:1 represents the deduced sequence of the-coding strand of a complementary DNA (cDNA) nucleic acid molecule denoted herein as neqFc$_\epsilon$R$\alpha_{1015}$, the production of which is disclosed in the Examples. The complement of SEQ ID NO:1 (represented herein by SEQ ID NO:3) refers to the nucleic acid sequence of the strand complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is complementary to (i.e., can form a complete double helix with) the strand for which the sequence is cited.

It should be noted that since nucleic acid sequencing technology is not entirely error-free, SEQ ID NO:1 and SEQ ID NO:3 (as well as other nucleic acid and protein sequences presented herein) represent apparent nucleic acid sequences of certain nucleic acid molecules encoding equine Fc$_\epsilon$R$\alpha$ proteins of the present invention.

In another embodiment, an equine Fc$_\epsilon$R$\alpha$ gene can be an allelic variant that includes a similar but not identical sequence to SEQ ID NO:1, SEQ ID NO:3, SEQ ID NO:4, SEQ ID NO:5, SEQ ID NO:6, SEQ ID NO:8 and/or SEQ ID NO:11. An allelic variant of an equine Fc$_\epsilon$R$\alpha$ gene is a gene that occurs at essentially the same locus (or loci) in the genome as the gene including SEQ ID NO:1, SEQ ID NO:3, SEQ ID NO:4, SEQ ID NO:5, SEQ ID NO:6, SEQ ID NO:8 and/or SEQ ID NO:11, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given horse since the genome is diploid and/or among a group of two or more horses. The present invention also includes variants due to laboratory manipulation, such as, but not limited to, variants produced during polymerase chain reaction amplification.

The minimal size of a Fc$_\epsilon$R$\alpha$ protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an equine Fc$_\epsilon$R$\alpha$ protein homolog of the present invention is from about 12 to about 18 nucleotides in length. Thus, the minimal size of an equine Fc$_\epsilon$R$\alpha$ protein homolog of the present invention is from about 4 to about 6 amino acids in length. There is no limit, other than a practical limit, on the maximal size of such a nucleic acid molecule in that the nucleic acid molecule can include a portion of a gene, an entire gene, multiple genes, or portions thereof. The preferred size of a protein encoded by a nucleic acid molecule of the present invention depends on whether a full-length, fusion, multivalent, or functional portion of such a protein is desired. Preferably, the preferred size of a protein encoded by a nucleic acid molecule of the present invention is a portion of the protein that binds to IgE which is about 30 amino acids, more preferably about 35 amino acids and even more preferably about 44 amino acids in length.

As used herein, an equine refers to any member of the horse family. Examples of horses from which to isolate equine Fc$_\epsilon$R$\alpha$ proteins of the present invention (including isolation of the natural protein or production of the protein by recombinant or synthetic techniques) include, but are not limited to domestic horses and wild horses, with domestic horses, including race horses being more preferred.

Suitable horse cells from which to isolate an equine Fc$_\epsilon$R$\alpha$ protein of the present invention include cells that have Fc$_\epsilon$R$\alpha$ proteins. Preferred horse cells from which to obtain an equine Fc$_\epsilon$R$\alpha$ protein of the present invention include basophil cells, mast cells, mastocytoma cells, dendritic cells, B lymphocytes, macrophages, eosinophils, and/or monocytes. An equine $Fc_\epsilon R\alpha$ of the present invention is preferably obtained from mastocytoma cells, mast cells or basophil cells.

The present invention also includes mimetopes of equine $Fc_\epsilon R\alpha$ proteins of the present invention. As used herein, a mimetope of an equine $Fc_\epsilon R\alpha$ protein of the present invention refers to any compound that is able to mimic the activity of such an equine $Fc_\epsilon R\alpha$ protein (e.g., ability to bind to IgE), often because the mimetope has a structure that mimics the equine $Fc_\epsilon R\alpha$ protein. It is to be noted, however, that the mimetope need not have a structure similar to an equine $Fc_\epsilon R\alpha$ protein as long as the mimetope functionally mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); synthetic or natural organic or inorganic molecules, including nucleic acids; and/or any other peptidomimetic compounds. Mimetopes of the present invention can be designed using computer-generated structures of equine $Fc_\epsilon R\alpha$ proteins of the present invention. Mimetopes can also be obtained by generating random samples of molecules, such as oligonucleotides, peptides or other organic molecules, and screening such samples by affinity chromatography techniques using the corresponding binding partner, (e.g., an equine IgE Fc domain or anti-equine $Fc_\epsilon R\alpha$ antibody). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modeling. The predicted mimetope structures can then be produced by, for example, chemical synthesis, recombinant DNA technology, or by isolating a mimetope from a natural source. Specific examples of equine $Fc_\epsilon R\alpha$ mimetopes include anti-idiotypic antibodies, oligonucleotides produced using Selex™ technology, peptides identified by random screening of peptide libraries and proteins identified by phage display technology. A preferred mimetope is a peptidomimetic compound that is structurally and/or functionally similar to an equine $Fc_\epsilon R\alpha$ protein of the present invention, particularly to the IgE Fc domain binding site of the equine $Fc_\epsilon R\alpha$ protein. As used herein, the Fc domain of an antibody refers to the portion of an immunoglobulin that has Fc receptor binding effector function. Typically, the Fc domain of an IgE comprises the CH2 and CH3 domains of the heavy chain constant region.

According to the present invention, an equine $Fc_\epsilon R\alpha$ molecule of the present invention refers to: an equine $Fc_\epsilon R\alpha$ protein, in particular a soluble equine $Fc_\epsilon R\alpha$ protein; an equine $Fc_\epsilon R\alpha$ homolog; an equine $Fc_\epsilon R\alpha$ mimetope; an equine $Fc_\epsilon R\alpha$ substrate analog; or an equine $Fc_\epsilon R\alpha$ peptide. Preferably, an equine $Fc_\epsilon R\alpha$ molecule binds to IgE.

One embodiment of an equine $Fc_\epsilon R\alpha$ protein of the present invention is a fusion protein that includes an equine $Fc_\epsilon R\alpha$ protein-containing domain attached to one or more fusion segments. Suitable fusion segments for use with the present invention include, but are not limited to, segments that can: enhance a protein's stability; act as an immunopotentiator to enhance an immune response against an equine $Fc_\epsilon R\alpha$ protein; and/or assist purification of an equine $Fc_\epsilon R\alpha$ protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the equine $Fc_\epsilon R\alpha$-containing domain of the protein and can be susceptible to cleavage in order to enable straight-forward recovery of an equine $Fc_\epsilon R\alpha$ protein. Fusion proteins are preferably produced by culturing a recombinant cell transformed with a fusion nucleic acid molecule that encodes a protein including the fusion segment attached to either the carboxyl and/or amino terminal end of an equine $Fc_\epsilon R\alpha$-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); a "tag" domain (e.g., at least a portion of β-galactosidase, a strep tag peptide, other domains that can be purified using compounds that bind to the domain, such as monoclonal antibodies); and/or a linker and enzyme domain (e.g., alkaline phosphatase domain connected to an equine $Fc_\epsilon R\alpha$ protein by a linker). More preferred fusion segments include metal binding domains, such as a poly-histidine segment; a maltose binding domain; a strep tag peptide, such as that available from Biometra in Tampa, Fla.; and a phage T7 S10 peptide.

A preferred equine $Fc_\epsilon R\alpha$ protein of the present invention is encoded by a nucleic acid molecule that hybridizes under stringent hybridization conditions with at least one of the following nucleic acid molecules: $neqFc_\epsilon R\alpha_{1015}$, $neqFc_\epsilon R\alpha_{765}$, $neqFc_\epsilon R\alpha_{708}$ and $neqFc_\epsilon R\alpha_{603}$. Preferably, the equine $Fc_\epsilon R\alpha$ protein binds to IgE. A further preferred isolated protein is encoded by a nucleic acid molecule that hybridizes under stringent hybridization conditions with a nucleic acid molecule having nucleic acid sequence SEQ ID NO:3, SEQ ID NO:5 and SEQ ID NO:8.

Translation of SEQ ID NO:1 suggests that nucleic acid molecule $neqFc_\epsilon R\alpha_{1015}$ encodes a full-length equine protein of about 255 amino acids, referred to herein as $PequFc_\epsilon R\alpha_{255}$, represented by SEQ ID NO:2, assuming an open reading frame having an initiation (start) codon spanning from nucleotide 12 through nucleotide 14 of SEQ ID NO:1 and a termination (stop) codon spanning from nucleotide 777 through nucleotide 779 of SEQ ID NO:1. The coding region encoding $PequFc_\epsilon R\alpha_{263}$ is represented by nucleic acid molecule $neqFc_\epsilon R\alpha_{765}$, having a coding strand with the nucleic acid sequence represented by SEQ ID NO:4 and a complementary strand with the nucleic acid sequence represented by SEQ ID NO:5. Analysis of SEQ ID NO:2 suggests the presence of a signal peptide encoded by a stretch of amino acids spanning from amino acid 1 through amino acid 19. The proposed mature protein, denoted herein as $PequFc_\epsilon R\alpha_{236}$, contains about 236 amino acids which is represented herein as SEQ ID NO:7. $PequFc_\epsilon R\alpha_{236}$ is encoded by nucleic acid molecule $neqFc_\epsilon R\alpha_{708}$, having a coding strand with the nucleic acid sequence represented by SEQ ID NO:6 and a complementary strand with the nucleic acid sequence represented by SEQ ID NO:8. The amino acid sequence of $PequFc_\epsilon R\alpha_{236}$ (i.e. SEQ ID NO:7) predicts that $PequFc_\epsilon R\alpha_{236}$ has an estimated molecular weight of about 27.3 kD, an estimated pI of about 9.77.

Comparison of amino acid sequence SEQ ID NO:2 (i.e., the amino acid sequence of $PequFc_\epsilon R\alpha_{255}$) with amino acid sequences reported in GenBank™ indicates that SEQ ID NO:2 showed the most homology, i.e., about 61% identity, with a human high affinity IgE receptor α-subunit (SwissProt accession number P12319).

More preferred equine $Fc_\epsilon R\alpha$ proteins of the present invention include proteins comprising amino acid sequences that are at least about 65%, preferably at least about 70%, more preferably at least about 75%, more preferably at least about 80%, more preferably at least about 85%, more preferably at least about 90% and even more preferably about 95%, identical to amino acid sequence SEQ ID NO:2, SEQ ID NO:7 and/or SEQ ID NO:12. Amino acid sequence analysis can be performed using either the DNAsis™ program (available from Hitachi Software, San Bruno, Calif.) or the MacVector™ program (available from the Eastman Kodak Company, New Haven, Conn.), preferably using default stringency parameters.

More preferred equine $Fc_\epsilon R\alpha$ proteins of the present invention include proteins encoded by a nucleic acid molecule comprising at least a portion of $neqFc_\epsilon R\alpha_{1015}$, $neqFc_\epsilon R\alpha_{765}$, $neqFc_\epsilon R\alpha_{708}$ and/or $neqFc_\epsilon R\alpha_{603}$, or of allelic variants of such nucleic acid molecules, the portion being capable of binding to IgE. More preferred is an equine $Fc_\epsilon R\alpha$ protein encoded by $neqFc_\epsilon R\alpha_{1015}$, $neqFc_\epsilon R\alpha_{765}$, $neqFc_\epsilon R\alpha_{708}$ and/or $neqFc_\epsilon R\alpha_{603}$, or by an allelic variant of such nucleic acid molecules. Particularly preferred equine $Fc_\epsilon R\alpha$ proteins are $PequFc_\epsilon R\alpha_{255}$, $PequFc_\epsilon R\alpha_{236}$ and $PequFc_\epsilon R\alpha_{201}$.

In one embodiment, a preferred equine $Fc_\epsilon R\alpha$ protein of the present invention is encoded by at least a portion of SEQ ID NO:1, SEQ ID NO:4, SEQ ID NO:6 and/or SEQ ID NO:11, and, as such, has an amino acid sequence that includes at least a portion of SEQ ID NO:2, SEQ ID NO:7 and/or SEQ ID NO:12.

Also preferred is an equine $Fc_\epsilon R\alpha$ protein encoded by an allelic variant of a nucleic acid molecule comprising at least a portion of SEQ ID NO:1, SEQ ID NO:4, SEQ ID NO:6 and/or SEQ ID NO:11. Particularly preferred equine $Fc_\epsilon R\alpha$ proteins of the present invention include SEQ ID NO:2, SEQ ID NO:7 and SEQ ID NO:12 (including, but not limited to, the proteins consisting of such sequences, fusion proteins and multivalent proteins) and proteins encoded by allelic variants of nucleic acid molecules that encode SEQ ID NO:2, SEQ ID NO:7 and SEQ ID NO:12.

Another embodiment of the present invention is an isolated nucleic acid molecule that hybridizes under stringent hybridization conditions with an equine $Fc_\epsilon R\alpha$ gene. The identifying characteristics of such a gene are heretofore described. A nucleic acid molecule of the present invention can include an isolated natural equine $Fc_\epsilon R\alpha$ gene or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with an equine $Fc_\epsilon R\alpha$ gene under stringent hybridization conditions.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated equine $Fc_\epsilon R\alpha$ nucleic acid molecule of the present invention can be isolated from its natural source or can be produced using recombinant DNA technology (e.g., polymerase chain reaction (PCR) amplification, cloning) or chemical synthesis. Isolated equine $Fc_\epsilon R\alpha$ nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode an equine $Fc_\epsilon R\alpha$ protein of the present invention or to form stable hybrids under stringent conditions with natural gene isolates.

An equine $Fc_\epsilon R\alpha$ nucleic acid molecule homolog can be produced using a number of methods known to those skilled in the art (see, for example, Sambrook et al., ibid.). For example, nucleic acid molecules can be modified using a variety of techniques including, but not limited to, classic mutagenesis and recombinant DNA techniques (e.g., site-directed mutagenesis, chemical treatment, restriction enzyme cleavage, ligation of nucleic acid fragments and/or PCR amplification), synthesis of oligonucleotide mixtures and ligation of mixture groups to "build" a mixture of nucleic acid molecules and combinations thereof. Nucleic acid molecule homologs can be selected by hybridization with an equine $Fc_\epsilon R\alpha$ gene or by screening for function of a protein encoded by the nucleic acid molecule (e.g., ability of an equine $Fc_\epsilon R\alpha$ protein to bind equine IgE).

An isolated nucleic acid molecule of the present invention can include a nucleic acid sequence that encodes at least one equine $Fc_\epsilon R\alpha$ protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an equine $Fc_\epsilon R\alpha$ protein.

One embodiment of the present invention is an equine $Fc_\epsilon R\alpha$ nucleic acid molecule that hybridizes under stringent hybridization conditions with nucleic acid molecule $neqFc_\epsilon R\alpha_{1015}$ and preferably with a nucleic acid molecule having nucleic acid sequence SEQ ID NO:1 and/or SEQ ID NO:3.

Comparison of nucleic acid sequence SEQ ID NO:1 (i.e., the nucleic acid sequence of the coding strand of $neqFc_\epsilon R\alpha_{1015}$) with nucleic acid sequences reported in GenBank indicates that SEQ ID NO:1 showed the most homology, i.e., about 75% identity to a human mRNA for immunoglobulin E receptor alpha chain gene (Accession number X06948).

Preferred equine $Fc_\epsilon R\alpha$ nucleic acid molecules include nucleic acid molecules having a nucleic acid sequence that is at least about 80%, preferably at least about 85%, more preferably at least about 90%, and even more preferably at least about 95% identical to nucleic acid sequence SEQ ID NO:1, SEQ ID NO:3, SEQ ID NO:4, SEQ ID NO:5, SEQ ID NO:6, SEQ ID NO:8 and/or SEQ ID NO:11. DNA sequence analysis can be performed using either the DNAsis™ program or the MacVector™ program, preferably using default stringency parameters.

Another preferred nucleic acid molecule of the present invention includes at least a portion of nucleic acid sequence SEQ ID NO:1, SEQ ID NO:3, SEQ ID NO:4, SEQ ID NO:5, SEQ ID NO:6, SEQ ID NO:8 and/or SEQ ID NO:11, that is capable of hybridizing to an equine $Fc_\epsilon R\alpha$ gene of the present invention, as well as allelic variants thereof. A more preferred nucleic acid molecule includes the nucleic acid sequence SEQ ID NO:1, SEQ ID NO:3, SEQ ID NO:4, SEQ ID NO:5, SEQ ID NO:6, SEQ ID NO:8 and/or SEQ ID NO:11, as well as allelic variants of such a nucleic acid molecule. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

Preferred equine $Fc_\epsilon R\alpha$ nucleic acid molecules also include nucleic acid molecules having a nucleic acid sequence that is at least about 80%, preferably at least about 85%, more preferably at least about 90%, and even more preferably at least about 95% identical to nucleic acid molecules neqFc$_\epsilon$R$\alpha_{1015}$, neqFc$_\epsilon$R$\alpha_{765}$, neqFc$_\epsilon$R$\alpha_{708}$ and/or neqFc$_\epsilon$R$\alpha_{603}$. Particularly preferred nucleic acid molecules include neqFc$_\epsilon$R$\alpha_{1015}$, neqFc$_\epsilon$R$\alpha_{765}$, neqFc$_\epsilon$R$\alpha_{708}$ and neqFc$_\epsilon$R$\alpha_{603}$.

The present invention also includes a nucleic acid molecule encoding a protein having at least a portion of SEQ ID NO:2, SEQ ID NO:7 and SEQ ID NO:12, including nucleic acid molecules that have been modified to accommodate codon usage properties of the cells in which such nucleic acid molecules are to be expressed.

Knowing the nucleic acid sequences of certain equine $Fc_\epsilon R\alpha$ nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain equine $Fc_\epsilon R\alpha$ nucleic acid molecules from other horses. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include equine basophil cell, mast cell, mastocytoma cell, dendritic cell, B lymphocyte, macrophage, eosinophil, and/or monocyte cDNA libraries as well as genomic DNA libraries. Similarly, preferred DNA sources to screen or from which to amplify nucleic acid molecules include equine basophil cells, mast cells, mastocytoma cells, dendritic cells, B lymphocytes, macrophages, eosinophils, and/or monocytes cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising equine $Fc_\epsilon R\alpha$ genes or other equine $Fc_\epsilon R\alpha$ nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules or therapeutic reagents to inhibit equine $Fc_\epsilon R\alpha$ protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of equine $Fc_\epsilon R\alpha$ nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with horses.

Suitable and preferred nucleic acid molecules to include in recombinant vectors of the present invention are as disclosed herein. Preferred nucleic acid molecules to include in recombinant vectors, and particularly in recombinant molecules, include $neqFc_\epsilon R\alpha_{1015}$, $neqFc_\epsilon R\alpha_{765}$, $neqFc_\epsilon R\alpha_{708}$ and $neqFc_\epsilon R\alpha_{603}$. A particularly preferred recombinant molecule of the present invention includes $pFB\text{-}neqFc_\epsilon R\alpha_{603}$, the production of which is described in the Examples section.

Recombinant molecules of the present invention may also (a) contain secretory signals (i.e., signal segment nucleic acid sequences) to enable an expressed equine $Fc_\epsilon R\alpha$ protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments, as well as natural signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include equine $Fc_\epsilon R\alpha$ nucleic acid molecules disclosed herein. Particularly preferred nucleic acid molecules with which to transform a cell include neq$Fc_\epsilon R\alpha_{1015}$, neq$Fc_\epsilon R\alpha_{765}$, neq$Fc_\epsilon R\alpha_{708}$ and neq$Fc_\epsilon R\alpha_{603}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing equine $Fc_\epsilon R\alpha$ proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), other insect, other animal and plant cells. Preferred host cells include bacterial, mycobacteria, yeast, parasite, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli,* including *E. coli* K-12 derivatives; *Salmonella typhi; Salmonella typhimurium*, including attenuated strains such as UK-$1_x$3987 and SR-$11_x$4072*; Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, $LMTK^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. A particularly preferred recombinant molecule includes pFB-neq$Fc_\epsilon R\alpha_{603}$.

A recombinant cell of the present invention includes any cell transformed with at least one of any nucleic acid molecule of the present invention. Suitable and preferred nucleic acid molecules as well as suitable and preferred recombinant molecules with which to transform cells are disclosed herein. A particularly preferred recombinant cell includes *S. frugiperda*:pFB-neq$Fc_\epsilon R\alpha_{603}$. Details regarding the production of this recombinant cell is disclosed herein.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated equine $Fc_\epsilon R\alpha$ proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce an equine $Fc_\epsilon R\alpha$ protein of the present invention. Such a medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial.

The present invention also includes isolated (i.e., removed from their natural milieu) antibodies that selectively bind to an equine $Fc_\epsilon R\alpha$ protein of the present invention or a mimetope thereof (i.e., anti-equine $Fc_\epsilon R\alpha$ antibodies). As used herein, the term "selectively binds to" an equine $Fc_\epsilon R\alpha$ protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid. An anti-equine $Fc_\epsilon R\alpha$ antibody preferably selectively binds to an equine $Fc_\epsilon R\alpha$ protein in such a way as to reduce the activity of that protein.

Isolated antibodies of the present invention can include antibodies in a bodily fluid (such as, but not limited to, serum), or antibodies that have been purified to varying degrees. Antibodies of the present invention can be polyclonal or monoclonal. Functional equivalents of such antibodies, such as antibody fragments and genetically-engineered antibodies (including single chain antibodies or chimeric antibodies that can bind to more than one epitope) are also included in the present invention.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce equine $Fc_\epsilon R\alpha$ proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as tools to detect Fc epsilon receptor in the presence or absence of IgE and/or (b) as tools to screen expression libraries and/or to recover desired proteins of the present invention from a mixture of proteins and other contaminants. Furthermore, antibodies of the present invention can be used to target cytotoxic agents to cells having Fc epsilon receptors such as those disclosed herein in order to directly kill such cells. Targeting can be accomplished by conjugating (i.e., stably joining) such antibodies to the cytotoxic agents using techniques known to those skilled in the art. Suitable cytotoxic agents are known to those skilled in the art. Antibodies of the present invention, including $Fc_\epsilon R\alpha$-binding portions thereof, can also be used, for example, to inhibit binding of IgE to Fc epsilon receptors, to produce anti-equine $Fc_\epsilon R\alpha$ idiotypic antibodies, to purify cells having equine $Fc_\epsilon R\alpha$ proteins, to stimulate intracellular signal transduction through an equine $Fc_\epsilon R\alpha$ and to identify cells having equine $Fc_\epsilon R\alpha$ proteins.

An equine $Fc_\epsilon R\alpha$ molecule of the present invention can include chimeric molecules comprising a portion of an equine $Fc_\epsilon R\alpha$ molecule that binds to an IgE and a second molecule that enables the chimeric molecule to be bound to a substrate in such a manner that the $Fc_\epsilon R\alpha$ molecule portion binds to IgE in essentially the same manner as a $Fc_\epsilon R\alpha$ molecule that is not bound to a substrate. An example of a suitable second molecule includes a portion of an immunoglobulin molecule or another ligand that has a suitable binding partner that can be immobilized on a substrate, e.g., biotin and avidin, or a metal-binding protein and a metal (e.g., His), or a sugar-binding protein and a sugar (e.g., maltose).

An equine $Fc_\epsilon R\alpha$ molecule of the present invention can include chimeric molecules comprising a portion of an equine Fc$_\epsilon$R$\alpha$ molecule that binds to an IgE and a second molecule, such as an enzyme, that enables the chimeric molecule to bind to IgE in essentially the same manner as a Fc$_\epsilon$R$\alpha$ molecule which does not include such a second molecule, and to hydrolyze a substrate in such a manner so as to give a detectable signal. An example of a suitable second molecule includes alkaline phosphatase, horse radish peroxidase or urease. In one embodiment an equine Fc$_\epsilon$R$\alpha$ chimeric molecule of the present invention comprises a protein encoded by a recombinant molecule comprising a nucleic acid molecule that encodes at least a portion of an equine Fc$_\epsilon$R$\alpha$ molecule that binds to an IgE, operatively linked to a nucleic acid molecule that encodes an enzyme, preferably alkaline phosphatase.

An equine Fc$_\epsilon$R$\alpha$ molecule of the present invention can be contained in a formulation, herein referred to as a Fc$_\epsilon$R$\alpha$ molecule formulation. For example, an equine Fc$_\epsilon$R$\alpha$ molecule can be combined with a buffer in which the equine Fc$_\epsilon$R$\alpha$ molecule is solubilized, and/or with a carrier. Suitable buffers and carriers are known to those skilled in the art. Examples of suitable buffers include any buffer in which an equine Fc$_\epsilon$R$\alpha$ molecule can function to selectively bind to IgE, such as, but not limited to, phosphate buffered saline, water, saline, phosphate buffer, bicarbonate buffer, HEPES buffer (N-2-hydroxyethylpiperazine-N'-2-ethanesulfonic acid buffered saline), TES buffer (Tris-EDTA buffered saline), Tris buffer and TAE buffer (Tris-acetate-EDTA). Examples of carriers include, but are not limited to, polymeric matrices, toxoids, and serum albumins, such as bovine serum albumin. Carriers can be mixed with equine Fc$_\epsilon$R$\alpha$ molecules or conjugated (i.e., attached) to equine Fc$_\epsilon$R$\alpha$ molecules in such a manner as to not substantially interfere with the ability of the equine Fc$_\epsilon$R$\alpha$ molecules to selectively bind to IgE.

An equine Fc$_\epsilon$R$\alpha$ protein of the present invention can be bound to the surface of a cell comprising the equine Fc$_\epsilon$R$\alpha$ protein. A preferred equine Fc$_\epsilon$R$\alpha$ protein-bearing cell includes a recombinant cell comprising a nucleic acid molecule encoding an equine Fc$_\epsilon$R$\alpha$ protein of the present invention. A more preferred recombinant cell of the present invention comprises a nucleic acid molecule that encodes at least one of the following proteins: PequFc$_\epsilon$R$\alpha_{255}$, PequFc$_\epsilon$R$\alpha_{236}$ and PequFc$_\epsilon$R$\alpha_{201}$. An even more preferred recombinant cell comprises a nucleic acid molecule including neqFc$_\epsilon$R$\alpha_{1015}$, neqFc$_\epsilon$R$\alpha_{765}$, neqFc$_\epsilon$R$\alpha_{708}$ and neqFc$_\epsilon$R$\alpha_{603}$ with a recombinant cell comprising a nucleic acid molecule comprising a nucleic acid sequence including SEQ ID NO:1, SEQ ID NO:4, SEQ ID NO:6 or SEQ ID NO:11, or a nucleic acid molecule comprising an allelic variant of a nucleic acid molecule comprising SEQ ID NO:1, SEQ ID NO:4, SEQ ID NO:6 or SEQ ID NO:11, being even more preferred.

In addition, an equine Fc$_\epsilon$R$\alpha$ molecule formulation of the present invention can include not only an equine Fc$_\epsilon$R$\alpha$ molecule but also one or more additional antigens or antibodies useful in detecting IgE. As used herein, an antigen refers to any molecule capable of being selectively bound by an antibody. As used herein, selective binding of a first molecule to a second molecule refers to the ability of the first molecule to preferentially bind (e.g., having higher affinity higher avidity) to the second molecule when compared to the ability of a first molecule to bind to a third molecule. The first molecule need not necessarily be the natural ligand of the second molecule. Examples of such antibodies include, but are not limited to, antibodies that bind selectively to the constant region of an IgE heavy (i.e., anti-IgE isotype antibody) or antibodies that bind selectively to an IgE having a specific antigen specificity (i.e., anti-IgE idiotypic antibody). Suitable anti-IgE antibodies for use in a formulation of the present invention are not capable of cross-linking two or more IgE antibodies. Preferred anti-IgE antibodies include Fab fragments of the antibodies (as defined in Janeway et al., ibid.). Examples of such antigens include any antigen known to induce the production of IgE. Preferred antigens include allergens and parasite antigens. Allergens include, but are not limited to, allergens ingested, inhaled or contacted by a horse. Allergens of the present invention are preferably derived from fungi, rusts, smuts, bacteria, trees, weeds, shrubs, grasses, wheat, corn, grains, hays, straws, oats, alfalfa, clovers, soybeans, yeasts, fleas, flies, mosquitos, mites, midges, biting gnats, lice, bees, wasps, ants, true bugs or ticks. A suitable biting gnat allergen includes an allergen derived from a gnat, in particular a gnat saliva antigen. A preferred gnat allergen includes a gnat saliva antigen, in particular a gnat saliva antigen derived from a gnat of the genus Culicoides. A suitable flea allergen includes an allergen derived from a flea, in particular flea saliva antigen. A preferred flea allergen includes a flea saliva antigen. Preferred flea saliva antigens include antigens such as those disclosed in PCT Patent Publication No. WO 96/11271, published Apr. 18, 1996, by Frank et al. (this publication is incorporated by reference herein in its entirety), with flea saliva products and flea saliva proteins being particularly preferred. According to the present invention, a flea saliva protein includes a protein produced by recombinant DNA methods, as well as proteins isolated by other methods disclosed in PCT Patent Publication No. WO 96/11271.

Preferred general allergens include those derived from grass, Meadow Fescue, curly dock, plantain, Mexican firebush, lamb's quarters, pigweed, ragweed, goldenrod, sorrel, legumes, dandelion, sage, elm, cocklebur, elder, walnut, maple, sycamore, hickory, aspen, pine, cottonwood, ash, birch, cedar, oak, mulberry, cockroach, Dermataphagoides, Alternaria, Aspergillus, Cladosporium, Fusarium, Helminthosporium, Mucor, Curvularia, Candida, Penicillium, Pullularia, Rhizopus and/or Tricophyton. More preferred general allergens include those derived from Johnson grass, Kentucky blue grass, meadow fescue, orchard grass, perennial rye grass, red top grass, timothy grass, Bermuda grass, salt grass, brome grass, curly dock, yellow dock, English plantain, Mexican firebush, lamb's quarters, rough pigweed, short ragweed, goldenrod, sheep sorrel, red clover, dandelion, wormwood sage, American elm, common cocklebur, box elder, marsh elder, black walnut, red maple, eastern sycamore, white pine, eastern cottonwood, green ash, river birch, red cedar, red oak, red mulberry, cockroach, grain smut, oat stem rust, wheat stem rust, *Dermataphagoides farinae, Alternaria alternata, Alternaria tenuis, Curvularia spicifera, Aspergillus fumigatus, Cladosporium herbarum, Fusarium vasinfectum, Helminthosporium sativum, Mucor recemosus, Penicillium notatum, Pullularia pullulans, Rhizopus nigricans* and/or *Tricophyton* spp. The term "derived from" refers to a natural allergen of such plants or organisms (i.e., an allergen directly isolated from such plants or organisms), as well as, non-natural allergens of such plants or organisms that posses at least one epitope capable of eliciting an immune response against an allergen (e.g., produced using recombinant DNA technology or by chemical synthesis). Preferred allergens include those that cause allergic respiratory diseases in equines, including, for example, chronic obstructive pulmonary disease, exercise induced pulmonary hemorrhage and inhalant-induced urticaria. Such allergens include, but are not limited to, molds, components of dust and components of feed.

One embodiment of the present invention is a method to detect IgE which includes the steps of: (a) contacting an isolated equine $Fc_\epsilon R\alpha$ molecule with a putative IgE-containing composition under conditions suitable for formation of an equine $Fc_\epsilon R\alpha$ molecule:IgE complex; and (b) detecting the presence of IgE by detecting the equine $Fc_\epsilon R\alpha$ molecule:IgE complex. Presence of such an equine $Fc_\epsilon R\alpha$ molecule:IgE complex indicates that the animal is producing IgE. Preferred IgE to detect using an equine $Fc_\epsilon R\alpha$ molecule include equine IgE, canine IgE, feline IgE and human IgE, with equine IgE being particularly preferred. The present method can further include the step of determining whether an IgE complexed with an equine $Fc_\epsilon R\alpha$ protein is heat labile. Preferably, a heat labile IgE is determined by incubating an IgE at about 56° C. for about 3 or about 4 hours. Without being bound by theory, the inventors believe that heat labile forms of IgE bind to certain allergens and non-heat labile forms of IgE bind to other types of allergens. As such, detection of heat labile IgE compared with non-heat labile IgE can be used to discriminate between allergen sensitivities.

As used herein, canine refers to any member of the dog family, including domestic dogs, wild dogs and zoo dogs. Examples of dogs include, but are not limited to, domestic dogs, wild dogs, foxes, wolves, jackals and coyotes. As used herein, feline refers to any member of the cat family, including domestic cats, wild cats and zoo cats. Examples of cats include, but are not limited to, domestic cats, wild cats, lions, tigers, leopards, panthers, cougars, bobcats, lynx, jaguars, cheetahs, and servals.

As used herein, the term "contacting" refers to combining or mixing, in this case a putative IgE-containing composition with an equine $Fc_\epsilon R\alpha$ molecule. Formation of a complex between an equine $Fc_\epsilon R\alpha$ molecule and an IgE refers to the ability of the equine $Fc_\epsilon R\alpha$ molecule to selectively bind to the IgE in order to form a stable complex that can be measured (i.e., detected). As used herein, the term selectively binds to an IgE refers to the ability of an equine $Fc_\epsilon R\alpha$ molecule of the present invention to preferentially bind to IgE, without being able to substantially bind to other antibody isotypes. Binding between an equine $Fc_\epsilon R\alpha$ molecule and an IgE is effected under conditions suitable to form a complex; such conditions (e.g., appropriate concentrations, buffers, temperatures, reaction times) as well as methods to optimize such conditions are known to those skilled in the art, and examples are disclosed herein. Examples of complex formation conditions are also disclosed in, for example, in Sambrook et al., ibid.

As used herein, the term "detecting complex formation" refers to determining if any complex is formed, i.e., assaying for the presence (i.e., existence) of a complex. If complexes are formed, the amount of complexes formed can, but need not be, determined. Complex formation, or selective binding, between equine $Fc_\epsilon R\alpha$ molecule and any IgE in the composition can be measured (i.e., detected, determined) using a variety of methods standard in the art (see, for example, Sambrook et al. ibid.), examples of which are disclosed herein.

In one embodiment, a putative IgE-containing composition of the present method includes a biological sample from an animal. A suitable biological sample includes, but is not limited to, a bodily fluid composition or a cellular composition. A bodily fluid refers to any fluid that can be collected (i.e., obtained) from an animal, examples of which include, but are not limited to, blood, serum, plasma, urine, tears, aqueous humor, cerebrospinal fluid (CSF), saliva, lymph, nasal secretions, tracheobronchial aspirates, milk, feces and fluids obtained through bronchial alveolar lavage. Such a composition of the present method can, but need not be, pretreated to remove at least some of the non-IgE isotypes of immunoglobulin and/or other proteins, such as albumin, present in the fluid. Such removal can include, but is not limited to, contacting the bodily fluid with a material, such as Protein G, to remove IgG antibodies and/or affinity purifying IgE antibodies from other components of the body fluid by exposing the fluid to, for example, Concanavalin A. In another embodiment, a composition includes collected bodily fluid that is pretreated to concentrate immunoglobulin contained in the fluid. For example, immunoglobulin contained in a bodily fluid can be precipitated from other proteins using ammonium sulfate. A preferred composition of the present method is serum.

In another embodiment, a IgE-containing composition of the present method includes a cell that produces IgE. Such a cell can have IgE bound to the surface of the cell and/or can secrete IgE. An example of such a cell includes myeloma cells. IgE can be bound to the surface of a cell either directly to the membrane of the cell or bound to a molecule (e.g., an antigen) bound to the surface of the cell.

A complex can be detected in a variety of ways including, but not limited to use of one or more of the following assays: an enzyme-linked immunoassay, a radioimmunoassay, a fluorescence immunoassay, a chemiluminescent assay, a lateral flow assay, an agglutination assay, a particulate-based assay (e.g., using particulates such as, but not limited to, magnetic particles or plastic polymers, such as latex or polystyrene beads), an immunoprecipitation assay, a Bio-Core™ assay (e.g., using colloidal gold) and an immunoblotting assay (e.g., a western blot). Such assays are well known to those skilled in the art. Assays can be used to give qualitative or quantitative results depending on how they are used. Some assays, such as agglutination, particulate separation, and immunoprecipitation, can be observed visually (e.g., either by eye or by a machines, such as a densitometer or spectrophotometer) without the need for a detectable marker. In other assays, conjugation (i.e., attachment) of a detectable marker to the equine $Fc_\epsilon R\alpha$ molecule or to a reagent that selectively binds to the equine $Fc_\epsilon R\alpha$ molecule or to the IgE being detected (described in more detail below) aids in detecting complex formation. Examples of detectable markers include, but are not limited to, a radioactive label, an enzyme, a fluorescent label, a chemiluminescent label, a chromophoric label or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase) and biotin-related compounds or avidin-related compounds (e.g., streptavidin or ImmunoPure® NeutrAvidin available from Pierce, Rockford, Ill.). According to the present invention, a detectable marker can be connected to an equine $Fc_\epsilon R\alpha$ molecule using, for example, chemical conjugation or recombinant DNA technology (e.g., connection of a fusion segment such as that described herein for a metal binding domain; an immunoglobulin binding; a sugar binding domain; and a "tag" domain). Preferably a carbohydrate group of the equine $Fc_\epsilon R\alpha$ molecule is chemically conjugated to biotin.

In one embodiment, a complex is detected by contacting a putative IgE-containing composition with an equine $Fc_\epsilon R\alpha$ molecule that is conjugated to a detectable marker. A suitable detectable marker to conjugate to an equine $Fc_\epsilon R\alpha$ molecule includes, but is not limited to, a radioactive label, a fluorescent label, an enzyme label, a chemiluminescent label, a chromophoric label or a ligand. A detectable marker is conjugated to an equine Fc$_\epsilon$R$\alpha$ molecule in such a manner as not to block the ability of the equine Fc$_\epsilon$R$\alpha$ molecule to bind to the IgE being detected. Preferably, a carbohydrate group of an equine Fc$_\epsilon$R$\alpha$ molecule is conjugated to biotin.

In another embodiment, an equine Fc$_\epsilon$R$\alpha$ molecule:IgE complex is detected by contacting a putative IgE-containing composition with an equine Fc$_\epsilon$R$\alpha$ molecule and then contacting the complex with an indicator molecule. Suitable indicator molecules of the present invention include molecules that can bind to either the equine Fc$_\epsilon$R$\alpha$ molecule or to the IgE antibody. As such, an indicator molecule can comprise, for example, an antigen, an antibody and a lectin, depending upon which portion of the equine Fc$_\epsilon$R$\alpha$ molecule:IgE complex is being detected. Preferred indicator molecules that are antibodies include, for example, anti-IgE antibodies and anti-equine Fc$_\epsilon$R$\alpha$ antibodies. Preferred lectins include those lectins that bind to high-mannose groups. More preferred lectins bind to high-mannose groups present on an equine Fc$_\epsilon$R$\alpha$ protein of the present invention produced in insect cells. An indicator molecule itself can be attached to a detectable marker of the present invention. For example, an antibody can be conjugated to biotin, horseradish peroxidase, alkaline phosphatase or fluorescein.

In one preferred embodiment, an equine Fc$_\epsilon$R$\alpha$ molecule:IgE complex is detected by contacting the complex with an indicator molecule that selectively binds to an equine Fc$_\epsilon$R$\alpha$ molecule of the present invention. Examples of such indicator molecule includes, but are not limited to, an antibody that selectively binds to an equine Fc$_\epsilon$R$\alpha$ molecule (referred to herein as an anti-equine Fc$_\epsilon$R$\alpha$ antibody) or a compound that selectively binds to a detectable marker conjugated to an equine Fc$_\epsilon$R$\alpha$ molecule. An equine Fc$_\epsilon$R$\alpha$ molecule conjugated to biotin is preferably detected using streptavidin.

In another preferred embodiment, an equine Fc$_\epsilon$R$\alpha$ molecule:IgE complex is detected by contacting the complex with indicator molecule that selectively binds to an IgE antibody (referred to herein as an anti-IgE reagent). Examples of such an anti-IgE antibody include, but are not limited to, a secondary antibody that is an anti-isotype antibody (e.g., an antibody that selectively binds to the constant region of an IgE), an antibody-binding bacterial surface protein (e.g., Protein A or Protein G), an antibody-binding cell (e.g., a B cell, a T cell, a natural killer cell, a polymorphonuclear leukocyte cell, a monocyte cell or a macrophage cell), an antibody-binding eukaryotic cell surface protein (e.g., a Fc receptor), and an antibody-binding complement protein. A preferred indicator molecule includes an anti-equine IgE antibody. As used herein, an anti-IgE antibody includes not only a complete antibody but also any subunit or portion thereof that is capable of selectively binding to an IgE heavy chain constant region. For example, an anti-IgE reagent can include an Fab fragment or a F(ab')$_2$ fragment, both of which are described in detail in Janeway et al., in *Immunobiology, the Immune System in Health and Disease*, Garland Publishing, Inc., New York, 1996 (which is incorporated herein by this reference in its entirety).

In one embodiment a complex can be formed and detected in solution. In another embodiment, a complex can be formed in which one or more members of the complex are immobilized on (e.g., coated onto) a substrate. Immobilization techniques are known to those skilled in the art. Suitable substrate materials include, but are not limited to, plastic, glass, gel, celluloid, paper, PVDF (poly-vinylidene-fluoride), nylon, nitrocellulose, and particulate materials such as latex, polystyrene, nylon, nitrocellulose, agarose and magnetic resin. Suitable shapes for substrate material include, but are not limited to, a well (e.g., microtiter dish well), a plate, a dipstick, a bead, a lateral flow apparatus, a membrane, a filter, a tube, a dish, a celluloid-type matrix, a magnetic particle, and other particulates. A particularly preferred substrate comprises an ELISA plate, a dipstick, a radioimmunoassay plate, agarose beads, plastic beads, latex beads, immunoblot membranes and immunoblot papers. In one embodiment, a substrate, such as a particulate, can include a detectable marker.

A preferred method to detect IgE is an immunosorbent assay. An immunoabsorbent assay of the present invention comprises a capture molecule and an indicator molecule. A capture molecule of the present invention binds to an IgE in such a manner that the IgE is immobilized to a substrate. As such, a capture molecule is preferably immobilized to a substrate of the present invention prior to exposure of the capture molecule to a putative IgE-containing composition. An indicator molecule of the present invention detects the presence of an IgE bound to a capture molecule. As such, an indicator molecule preferably is not immobilized to the same substrate as a capture molecule prior to exposure of the capture molecule to a putative IgE-containing composition.

A preferred immunoabsorbent assay method includes a step of either: (a) immobilizing an equine Fc$_\epsilon$R$\alpha$ molecule on a substrate prior to contacting an equine Fc$_\epsilon$R$\alpha$ molecule with a putative IgE-containing composition to form an equine Fc$_\epsilon$R$\alpha$ molecule-immobilized substrate; and (b) binding a putative IgE-containing composition on a substrate prior to contacting an equine Fc$_\epsilon$R$\alpha$ molecule with a putative IgE-containing composition to form a putative IgE-containing composition-bound substrate. Preferably, the substrate includes a non-coated substrate, an equine Fc$_\epsilon$R$\alpha$ molecule-immobilized substrate, an antigen-immobilized substrate or an anti-IgE antibody-immobilized substrate.

Both a capture molecule and an indicator molecule of the present invention are capable of binding to an IgE. Preferably, a capture molecule binds to a different region of an IgE than an indicator molecule, thereby allowing a capture molecule to be bound to an IgE at the same time as an indicator molecule. The use of a reagent as a capture molecule or an indicator molecule depends upon whether the molecule is immobilized to a substrate when the molecule is exposed to an IgE. For example, an equine Fc$_\epsilon$R$\alpha$ molecule of the present invention is used as a capture molecule when the equine Fc$_\epsilon$R$\alpha$ molecule is bound on a substrate. Alternatively, an equine Fc$_\epsilon$R$\alpha$ molecule is used as an indicator molecule when the equine Fc$_\epsilon$R$\alpha$ molecule is not bound on a substrate. Suitable molecules for use as capture molecules or indicator molecules include, but are not limited to, an equine Fc$_\epsilon$R$\alpha$ molecule of the present invention, an antigen reagent or an anti-IgE antibody reagent of the present invention.

An immunoabsorbent assay of the present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be selected by those of skill in the art. Preferred secondary molecules of the present invention include an antigen, an anti-IgE idiotypic antibody and an anti-IgE isotypic antibody. Preferred tertiary molecules can be selected by a skilled artisan based upon the characteristics of the secondary molecule. The same strategy is applied for subsequent layers.

In one embodiment, a specific antigen is used as a capture molecule by being immobilized on a substrate, such as a microtiter dish well or a dipstick. Preferred antigens include those disclosed herein. A biological sample collected from an animal is applied to the substrate and incubated under conditions suitable (i.e., sufficient) to allow for antigen:IgE complex formation bound to the substrate (i.e., IgE in a sample binds to an antigen immobilized on a substrate). Excess non-bound material (i.e., material from the biological sample that has not bound to the antigen), if any, is removed from the substrate under conditions that retain antigen:IgE complex binding to the substrate. Preferred conditions are generally disclosed in Sambrook et al., ibid. An indicator molecule that can selectively bind to an IgE bound to the antigen is added to the substrate and incubated to allow formation of a complex between the indicator molecule and the antigen:IgE complex. Excess indicator molecule is removed, a developing agent is added if required, and the substrate is submitted to a detection device for analysis. A preferred indicator molecule for this embodiment is an equine $Fc_\epsilon R\alpha$ molecule, preferably conjugated to biotin, to a fluorescent label or to an enzyme label.

In one embodiment, an equine $Fc_\epsilon R\alpha$ molecule is used as a capture molecule by being immobilized on a substrate, such as a microtiter dish well or a dipstick. A biological sample collected from an animal is applied to the substrate and incubated under conditions suitable to allow for equine $Fc_\epsilon R\alpha$ molecule:IgE complex formation bound to the substrate. Excess non-bound material, if any, is removed from the substrate under conditions that retain equine $Fc_\epsilon R\alpha$ molecule:IgE complex binding to the substrate. An indicator molecule that can selectively bind to an IgE bound to the equine $Fc_\epsilon R\alpha$ molecule is added to the substrate and incubated to allow formation of a complex between the indicator molecule and the equine $Fc_\epsilon R\alpha$ molecule:IgE complex. Preferably, the indicator molecule is conjugated to a detectable marker (preferably to an enzyme label, to a colorimetric label, to a fluorescent label, to a radioisotope, or to a ligand such as of the biotin or avidin family). Excess indicator molecule is removed, a developing agent is added if required, and the substrate is submitted to a detection device for analysis. A preferred indicator molecule for this embodiment is an antigen that will bind to IgE in the biological sample or an anti-IgE isotype or idiotype antibody, either preferably being conjugated to fluorescein or biotin.

In one embodiment, an anti-IgE antibody (e.g., isotype or idiotype specific antibody) is used as a capture molecule by being immobilized on a substrate, such as a microtiter dish well or a dipstick. A biological sample collected from an animal is applied to the substrate and incubated under conditions suitable to allow for anti-IgE antibody:IgE complex formation bound to the substrate. Excess non-bound material, if any, is removed from the substrate under conditions that retain anti-IgE antibody:IgE complex binding to the substrate. An equine $Fc_\epsilon R\alpha$ molecule is added to the substrate and incubated to allow formation of a complex between the equine $Fc_\epsilon R\alpha$ molecule and the anti-IgE antibody:IgE complex. Preferably, the equine $Fc_\epsilon R\alpha$ molecule is conjugated to a detectable marker (preferably to biotin, an enzyme label or a fluorescent label). Excess equine $Fc_\epsilon R\alpha$ molecule is removed, a developing agent is added if required, and the substrate is submitted to a detection device for analysis.

In one embodiment, an immunosorbent assay of the present invention does not utilize a capture molecule. In this embodiment, a biological sample collected from an animal is applied to a substrate, such as a microtiter dish well or a dipstick, and incubated under conditions suitable to allow for IgE binding to the substrate. Any IgE present in the bodily fluid is immobilized on the substrate. Excess non-bound material, if any, is removed from the substrate under conditions that retain IgE binding to the substrate. An equine $Fc_\epsilon R\alpha$ molecule is added to the substrate and incubated to allow formation of a complex between the equine $Fc_\epsilon R\alpha$ molecule and the IgE. Preferably, the equine $Fc_\epsilon R\alpha$ molecule is conjugated to a detectable marker (preferably to biotin, an enzyme label or a fluorescent label). Excess equine $Fc_\epsilon R\alpha$ molecule is removed, a developing agent is added if required, and the substrate is submitted to a detection device for analysis.

Another preferred method to detect IgE is a lateral flow assay, examples of which are disclosed in U.S. Pat. No. 5,424,193, issued Jun. 13, 1995, by Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al.; each of these patent publications is incorporated by reference herein in its entirety. In one embodiment, a biological sample is placed in a lateral flow apparatus that includes the following components: (a) a support structure defining a flow path; (b) a labeling reagent comprising a bead conjugated to an antigen, the labeling reagent being impregnated within the support structure in a labeling zone; and (c) a capture reagent comprising an IgE-binding composition. Preferred antigens include those disclosed herein. The capture reagent is located downstream of the labeling reagent within a capture zone fluidly connected to the labeling zone in such a manner that the labeling reagent can flow from the labeling zone into the capture zone. The support structure comprises a material that does not impede the flow of the beads from the labeling zone to the capture zone. Suitable materials for use as a support structure include ionic (i.e., anionic or cationic) material. Examples of such a material include, but are not limited to, nitrocellulose (NC), PVDF, carboxymethylcellulose (CM). The support structure defines a flow path that is lateral and is divided into zones, namely a labeling zone and a capture zone. The apparatus can further comprise a sample receiving zone located along the flow path, more preferably upstream of the labeling reagent. The flow path in the support structure is created by contacting a portion of the support structure downstream of the capture zone, preferably at the end of the flow path, to an absorbent capable of absorbing excess liquid from the labeling and capture zones.

In this embodiment, the biological sample is applied to the sample receiving zone which includes a portion of the support structure. The labeling zone receives the sample from the sample receiving zone which is directed downstream by the flow path. The labeling zone comprises the labeling reagent that binds to IgE. A preferred labeling reagent is an antigen conjugated, either directly or through a linker, to a plastic bead substrate, such as to a latex bead. The substrate also includes a detectable marker, preferably a colorimetric marker. Typically, the labeling reagent is impregnated to the support structure by drying or lyophilization. The sample structure also comprises a capture zone downstream of the labeling zone. The capture zone receives labeling reagent from the labeling zone which is directed downstream by the flow path. The capture zone contains the capture reagent, in this case an equine $Fc_\epsilon R\alpha$ molecule, as disclosed above, that immobilizes the IgE complexed to the antigen in the capture zone. The capture reagent is preferably fixed to the support structure by drying or lyophilizing. The labeling reagent accumulates in the capture zone and the accumulation is assessed visually or by an optical detection device.

In another embodiment, a lateral flow apparatus used to detect IgE includes: (a) a support structure defining a flow path; (b) a labeling reagent comprising an equine $Fc_\epsilon R\alpha$ molecule as described above, the labeling reagent impregnated within the support structure in a labeling zone; and (c) a capture reagent comprising an antigen, the capture reagent being located downstream of the labeling reagent within a capture zone fluidly connected to the labeling zone in such a manner that the labeling reagent can flow from the labeling zone into the capture zone. The apparatus preferably also includes a sample receiving zone located along the flow path, preferably upstream of the labeling reagent. The apparatus preferably also includes an absorbent located at the end of the flow path.

One embodiment of the present invention is an inhibition assay in which the presence of IgE in a putative IgE-containing composition is determined by adding such composition to an equine $Fc_\epsilon R\alpha$ molecule of the present invention and an isolated IgE known to bind to the equine $Fc_\epsilon R\alpha$ molecule. The absence of binding of the equine $Fc_\epsilon R\alpha$ molecule to the known IgE indicates the presence of IgE in the putative IgE-containing composition. The known IgE is preferably conjugated to a detectable marker.

The present invention also includes kits to detect IgE based on each of the disclosed detection methods. One embodiment is a kit to detect IgE comprising an equine $Fc_\epsilon R\alpha$ protein and a means for detecting an IgE. Suitable and preferred equine $Fc_\epsilon R\alpha$ protein are disclosed herein. Suitable means of detection include compounds disclosed herein that bind to either the equine $Fc_\epsilon R\alpha$ protein or to an IgE. A preferred kit of the present invention further comprises a detection means including one or more antigens disclosed herein, an antibody capable of selectively binding to an IgE disclosed herein and/or a compound capable of binding to a detectable marker conjugated to an equine $Fc_\epsilon R\alpha$ protein (e.g., avidin, streptavidin and ImmunoPure® NeutrAvidin when the detectable marker is biotin). Such antigens preferably induce IgE antibody production in animals including equines, canines and/or felines.

Another preferred kit of the present invention is a general allergen kit comprising an allergen common to all regions of the United States and an equine $Fc_\epsilon R\alpha$ protein of the present invention. As used herein, a "general allergen" kit refers to a kit comprising allergens that are found substantially throughout the United States (i.e., essentially not limited to certain regions of the United States). A general allergen kit provides an advantage over regional allergen kits because a single kit can be used to test an animal located in most geographical locations on the United States. Suitable and preferred general allergens for use with a general allergen kit of the present invention include those general allergens disclosed herein.

Another preferred kit of the present invention is a feed and/or feed dust allergen kit comprising a feed and/or feed dust allergen including wheat, corn, alfalfa, hay, straw, oats, grains, processed grain by-products and grasses and/or dusts thereof, and an equine $Fc_\epsilon R\alpha$ molecule of the present invention. Kits for detecting hypersensitivity to feeds and/or feed dust allergens can be used in combination with a mold allergen which commonly occurs on such feeds.

A preferred kit of the present invention includes those in which the allergen is immobilized on a substrate. If a kit comprises two or more antigens, the kit can comprise one or more compositions, each composition comprising one antigen. As such, each antigen can be tested separately. A kit can also contain two or more diagnostic reagents for IgE, additional isolated IgE antigens and/or antibodies as disclosed herein. Particularly preferred are kits used in a lateral flow assay format. It is within the scope of the present invention that a lateral flow assay kit can include one or more lateral flow assay apparatuses. Multiple lateral flow apparatuses can be attached to each other at one end of each apparatus, thereby creating a fan-like structure.

In particular, a method and kit of the present invention are useful for diagnosing abnormal conditions in animals that are associated with changing levels of IgE. Particularly preferred conditions to diagnose include allergies, parasitic infections and neoplasia. For example, a method and kit of the present invention are particularly useful for detecting hypersensitivity to the bite of gnats of the genus Culicoides when such method or kit includes the use of a Culicoides antigen. Preferably, a putative IgE-containing composition is obtained from an animal suspected of being hypersensitive to Culicoides bites. A method and kit of the present invention are also useful for detecting flea allergy dermatitis (FAD), when such method or kit includes the use of flea antigens, preferably flea saliva antigens. FAD is defined as a hypersensitive response to fleabites. Preferably, a putative IgE-containing composition is obtained from an animal suspected of having FAD. Preferred animals include those disclosed herein, with horses, dogs and cats being more preferred.

One embodiment of the present invention is a therapeutic composition that, when administered to an animal in an effective manner, is capable of reducing Fc receptor mediated reactions associated with diseases related to biological responses involving Fc receptor function. A therapeutic composition of the present invention can include: an isolated equine $Fc_\epsilon R\alpha$ protein, or homolog thereof; a mimetope of an equine $Fc_\epsilon R\alpha$ protein; an isolated nucleic acid molecule that hybridizes under stringent hybridization conditions with an equine $Fc_\epsilon R\alpha$ gene; an isolated antibody that selectively binds to an equine $Fc_\epsilon R\alpha$ protein; and/or an inhibitor that interferes with formation of a complex between an equine $Fc_\epsilon R\alpha$ protein and IgE.

One embodiment of a therapeutic composition of the present invention is a therapeutic compound comprising an equine $Fc_\epsilon R\alpha$ molecule of the present invention, that binds to an IgE. According to the present invention, an equine $Fc_\epsilon R\alpha$ molecule competes for IgE with naturally-occurring Fc epsilon receptors, particularly those on mastocytoma cells, mast cells or basophils, so that IgE is bound to the administered equine $Fc_\epsilon R\alpha$ molecule and thus is unable to bind to Fc epsilon receptor on a cell, thereby inhibiting mediation of a biological response. Preferred equine $Fc_\epsilon R\alpha$ molecule for use in a therapeutic composition comprises an equine $Fc_\epsilon R\alpha$ protein, or homolog thereof, as described herein, particularly a fragment thereof, which binds to IgE. Equine $Fc_\epsilon R\alpha$ molecules for use in a therapeutic composition can be in a monovalent and/or multivalent form, so long as the equine $Fc_\epsilon R\alpha$ molecule is capable of binding to IgE. A more preferred equine $Fc_\epsilon R\alpha$ molecule for use in a therapeutic composition includes a soluble fragment of an equine $Fc_\epsilon R\alpha$ protein. A preferred equine $Fc_\epsilon R\alpha$ protein is encoded by $neqFc_\epsilon R\alpha_{603}$ and an even more preferred equine $Fc_\epsilon R\alpha$ protein is $PequFc_\epsilon R\alpha_{201}$.

Examples of suitable nucleic acid molecules for use in a therapeutic composition of the present invention are disclosed herein.

Another embodiment of a therapeutic composition of the present invention comprises a therapeutic compound that interferes with the formation of a complex between equine $Fc_\epsilon R\alpha$ protein and IgE, usually by binding to or otherwise interacting with or otherwise modifying the equine $Fc_\epsilon R\alpha$ protein's IgE binding site. Equine $Fc_\epsilon R\alpha$ protein inhibitors can also interact with other regions of the equine $Fc_\epsilon R\alpha$ protein to inhibit equine $Fc_\epsilon R\alpha$ protein activity, for example, by allosteric interaction. An inhibitor of an equine $Fc_\epsilon R\alpha$ protein can interfere with $Fc_\epsilon R\alpha$ protein and IgE complex formation by, for example, preventing formation of a $Fc_\epsilon R\alpha$ protein and IgE complex or disrupting an existing $Fc_\epsilon R\alpha$ protein and IgE complex causing the $Fc_\epsilon R\alpha$ protein and IgE to dissociate. An inhibitor of an equine $Fc_\epsilon R\alpha$ protein is usually a relatively small molecule. Preferably, an equine $Fc_\epsilon R\alpha$ protein inhibitor of the present invention is identified by its ability to bind to, or otherwise interact with, an equine $Fc_\epsilon R\alpha$ protein, thereby interfering with the formation of a complex between an equine $Fc_\epsilon R\alpha$ protein and IgE.

Preferred inhibitors of an equine $Fc_\epsilon R\alpha$ protein of the present invention include, but are not limited to, a substrate analog of an equine $Fc_\epsilon R\alpha$ protein, a mimetope of an equine $Fc_\epsilon R\alpha$ protein, a soluble (i.e., secreted form of an equine $Fc_\epsilon R\alpha$ protein) portion of an equine $Fc_\epsilon R\alpha$ protein that binds to IgE, and other molecules that bind to an equine $Fc_\epsilon R\alpha$ protein (e.g., to an allosteric site) in such a manner that IgE-binding activity of the equine $Fc_\epsilon R\alpha$ protein is inhibited. An equine $Fc_\epsilon R\alpha$ protein substrate analog refers to a compound that interacts with (e.g., binds to, associates with, modifies) the IgE-binding site of an equine $Fc_\epsilon R\alpha$ protein. A preferred equine $Fc_\epsilon R\alpha$ protein substrate analog inhibits IgE-binding activity of an equine $Fc_\epsilon R\alpha$ protein. Equine $Fc_\epsilon R\alpha$ protein substrate analogs can be of any inorganic or organic composition, and, as such, can be, but are not limited to, peptides, nucleic acids, and peptidomimetic compounds. Equine $Fc_\epsilon R\alpha$ protein substrate analogs can be, but need not be, structurally similar to an equine $Fc_\epsilon R\alpha$ protein's natural substrate (e.g., IgE) as long as they can interact with the active site (e.g., IgE-binding site of that equine $Fc_\epsilon R\alpha$). Equine $Fc_\epsilon R\alpha$ protein substrate analogs can be designed using computer-generated structures of equine $Fc_\epsilon R\alpha$ proteins of the present invention or computer structures of, for example, the Fc domain of IgE. Substrate analogs can also be obtained by generating random samples of molecules, such as oligonucleotides, peptides, peptidomimetic compounds, or other inorganic or organic molecules, and screening such samples by affinity chromatography techniques using the corresponding binding partner, (e.g., an equine $Fc_\epsilon R\alpha$ protein or anti-equine $Fc_\epsilon R\alpha$ idiotypic antibody). A preferred equine $Fc_\epsilon R\alpha$ protein substrate analog is a peptidomimetic compound (i.e., a compound that is structurally and/or functionally similar to a natural substrate of an equine $Fc_\epsilon R\alpha$ protein of the present invention, particularly to the region of the substrate that binds to an equine $Fc_\epsilon R\alpha$ protein, but that inhibits IgE binding upon interacting with the IgE binding site).

Equine $Fc_\epsilon R\alpha$ molecules, as well as other inhibitors and therapeutic compounds, can be used directly as compounds in compositions of the present invention to treat animals as long as such compounds are not harmful to the animals being treated.

The present invention also includes a therapeutic composition comprising one or more therapeutic compounds of the present invention. Examples of such therapeutic compounds are disclosed herein.

In one embodiment, a therapeutic composition of the present invention can be used to reduce a Fc epsilon receptor-mediated biological response in an animal by administering such a composition to an animal. Preferably, an animal is treated by administering to the animal a therapeutic composition of the present invention in such a manner that a therapeutic compound (e.g., an inhibitor of an equine $Fc_\epsilon R\alpha$ protein, an anti-equine $Fc_\epsilon R\alpha$ antibody, an inhibitor of IgE, or nucleic acid molecules encoding equine $Fc_\epsilon R\alpha$ proteins) binds to an IgE or a Fc epsilon receptor in the animal. Such administration could be by a variety of routes known to those skilled in the art including, but not limited to, subcutaneous, intradermal, intravenous, intranasal, oral, aerosol, transdermal, intramuscular routes and other parenteral routes.

Compositions of the present invention can be administered to any animal having a Fc epsilon receptor or an IgE that binds to a therapeutic compound of the present invention or to a protein expressed by a nucleic acid molecule contained in a therapeutic composition. Preferred animals to treat include mammals and birds, with horses, dogs, cats, humans and other pets, work and/or economic food animals. Particularly preferred animals to protect are horses, cats and dogs.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of an animal at a constant rate sufficient to attain therapeutic dose levels of the composition to reduce Fc epsilon receptor-mediated biological responses in the animal. As used herein, a Fc epsilon receptor-mediated biological response refers to cellular responses that occur when Fc epsilon receptor is complexed with IgE. For example, a Fc epsilon receptor-mediated biological response includes release of biological mediators, such as histamine, prostaglandins and/or proteases, that can trigger clinical symptoms of allergy. The therapeutic composition is preferably released over a period of time ranging from about 1 to about 12 months. A preferred controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Acceptable protocols to administer therapeutic compositions of the present invention in an effective manner include individual dose size, number of doses, frequency of dose administration, and mode of administration. Determination of such protocols can be accomplished by those skilled in the art. A suitable single dose is a dose that is capable of protecting (i.e., preventing or treating) an animal from disease when administered one or more times over a suitable time period. The need for additional administrations of a therapeutic composition can be determined by one of skill in the art in accordance with the given condition of a patient. For example, to regulate an antigen-specific Fc epsilon receptor-mediated response, a therapeutic composition may be administered more frequently when an antigen is present in a patient's environment in high amounts and less frequently when the antigen is present in lower amounts.

According to one embodiment, a nucleic acid molecule of the present invention can be administered to an animal in a fashion to enable expression of that nucleic acid molecule into an equine $Fc_\epsilon R\alpha$ protein or an equine $Fc_\epsilon R\alpha$ RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid molecule (e.g., as naked DNA or RNA molecules, such as is taught, for example in Wolff et al., 1990, *Science* 247, 1465–1468) or (b) administering a nucleic acid molecule packaged as a recombinant virus or as a recombinant cell (i.e., the nucleic acid molecule is delivered by a viral or cellular vehicle).

A naked nucleic acid molecule of the present invention includes a nucleic acid molecule of the present invention and preferably includes a recombinant molecule of the present invention that preferably is replication, or otherwise amplification, competent. A naked nucleic acid of the present invention can comprise one or more nucleic acid molecules of the present invention in the form of, for example, a bicistronic recombinant molecule having, for example one or more internal ribosome entry sites. Preferred naked nucleic acid molecules include at least a portion of a viral genome (i.e., a viral vector). Preferred viral vectors include those based on alphaviruses, poxviruses, adenoviruses, herpesviruses, picornaviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid molecules of the present invention can be administered by a variety of methods. Suitable delivery methods include, for example, intramuscular injection, subcutaneous injection, intradermal injection, intradermal scarification, particle bombardment, oral application, and nasal application, with intramuscular injection, intradermal injection, intradermal scarification and particle bombardment being preferred. A preferred single dose of a naked DNA molecule ranges from about 1 nanogram (ng) to about 1 milligram (mg), depending on the route of administration and/or method of delivery, as can be determined by those skilled in the art. Examples of administration methods are disclosed, for example, in U.S. Pat. No. 5,204,253, by Bruner, et al., issued Apr. 20, 1993, PCT Publication No. WO 95/19799, published Jul. 27, 1995, by McCabe, and PCT Publication No. WO 95/05853, published Mar. 2, 1995, by Carson, et al. Naked DNA molecules of the present invention can be contained in an aqueous excipient (e.g., phosphate buffered saline) and/or with a carrier (e.g., lipid-based vehicles), or it can be bound to microparticles (e.g., gold particles).

A recombinant virus of the present invention includes a recombinant molecule of the present invention that is packaged in a viral coat and that can be expressed in an animal after administration. Preferably, the recombinant molecule is packaging-deficient and/or encodes an attenuated virus. A number of recombinant viruses can be used, including, but not limited to, those based on alphaviruses, poxviruses, adenoviruses, herpesviruses, picornaviruses and retroviruses. Preferred recombinant viruses are those based on alphaviruses (such as Sindbis virus), raccoon poxviruses, species-specific herpesviruses and species-specific poxviruses. An example of methods to produce and use alphavirus recombinant virus is disclosed in PCT Publication No. WO 94/17813, by Xiong et al., published Aug. 18, 1994, which is incorporated by reference herein in its entirety.

When administered to an animal, a recombinant virus of the present invention infects cells within the recipient animal and directs the production of a protein or RNA nucleic acid molecule that is capable of reducing Fc epsilon receptor-mediated biological responses in the animal. For example, a recombinant virus comprising an equine $Fc_{\epsilon}R\alpha$ nucleic acid molecule of the present invention is administered according to a protocol that results in the animal producing an amount of protein or RNA sufficient to reduce Fc epsilon receptor-mediated biological responses. A preferred single dose of a recombinant virus of the present invention is from about $1\times10^4$ to about $1\times10^7$ virus plaque forming units (pfu) per kilogram body weight of the animal. Administration protocols are similar to those described herein for protein-based compositions, with subcutaneous, intramuscular, intranasal and oral administration routes being preferred.

A recombinant cell useful in a therapeutic composition of the present invention includes recombinant cells of the present invention that comprises at least one equine $Fc_{\epsilon}R\alpha$ of the present invention. Preferred recombinant cells for this embodiment include Salmonella, *E. coli,* Listeria, Mycobacterium, *S. frugiperda*, yeast, (including *Saccharomyces cerevisiae*), BHK, CV-1, myoblast G8, COS (e.g., COS-7), Vero, MDCK and CRFK recombinant cells. A recombinant cell of the present invention can be administered in a variety of ways but have the advantage that they can be administered orally, preferably at doses ranging from about $10^8$ to about $10^{12}$ cells per kilogram body weight. Administration protocols are similar to those described herein for protein compositions. Recombinant cells can comprise whole cells, cells stripped of cell walls or cell lysates.

One embodiment of the present invention is a method of immunotherapy comprising the steps of: (a) administering to an animal an effective amount of a therapeutic composition selected from the group consisting of an inhibitor of an equine $Fc_{\epsilon}R\alpha$ and an equine $Fc_{\epsilon}R\alpha$ protein (including homologs), wherein said equine $Fc_{\epsilon}R\alpha$ is capable of binding to IgE. Suitable therapeutic compositions and methods of administration methods are disclosed herein. According to the present invention, a therapeutic composition and method of the present invention can be used to prevent or alleviate symptoms associated with Fc epsilon receptor-mediated biological responses.

The efficacy of a therapeutic composition of the present invention to effect Fc epsilon receptor-mediated biological responses can be tested using standard methods for detecting Fc receptor-mediated immunity including, but not limited to, immediate hypersensitivity, delayed hypersensitivity, antibody-dependent cellular cytotoxicity (ADCC), immune complex activity, mitogenic activity, histamine release assays and other methods such as those described in Janeway et al., ibid.

An inhibitor of equine $Fc_{\epsilon}R\alpha$ activity can be identified using equine $Fc_{\epsilon}R\alpha$ proteins of the present invention by determining the ability of an inhibitor to prevent or disrupt complex formation between an equine $Fc_{\epsilon}R\alpha$ protein and IgE. One embodiment of the present invention is a method to identify a compound capable of inhibiting equine $Fc_{\epsilon}R\alpha$ activity. Such a method includes the steps of (a) contacting (e.g., combining, mixing) an isolated equine $Fc_{\epsilon}R\alpha$ protein with a putative inhibitory compound under conditions in which, in the absence of the compound, the equine $Fc_{\epsilon}R\alpha$ protein has IgE binding activity, and (b) determining if the putative inhibitory compound inhibits the IgE binding activity. Putative inhibitory compounds to screen include small organic molecules, antibodies (including mimetopes thereof) and substrate analogs. Methods to determine IgE binding activity are known to those skilled in the art.

The present invention also includes a test kit to identify a compound capable of inhibiting equine $Fc_{\epsilon}R\alpha$ activity. Such a test kit includes: an isolated equine $Fc_{\epsilon}R\alpha$ protein having IgE binding activity or a complex of equine $Fc_{\epsilon}R\alpha$ protein and IgE; and a means for determining the extent of inhibition of IgE binding activity in the presence of (i.e., effected by) a putative inhibitory compound. Such compounds are also screened to identify those that are substantially not toxic in animals.

The following examples are provided for the purposes of illustration and are not intended to limit the scope of the present invention.

EXAMPLES

It is to be noted that the Examples include a number of molecular biology, microbiology, immunology and biochemistry techniques considered to be known to those skilled in the art. Disclosure of such techniques can be found, for example, in Sambrook et al., ibid., and related references.

Example 1

This example describes the isolation, by DNA hybridization, of a nucleic acid molecule encoding a $Fc_{\epsilon}R\alpha$ chain from *Equus caballus.*

This nucleic acid molecule was isolated from a horse buffy coat cDNA library by its ability to hybridize with a $^{32}$P-labeled cDNA encoding the human $Fc_{\epsilon}R\alpha$ chain (Kochan et al., *Nucleic Acids Res.* 16:3584, 1988). The horse buffy coat cDNA library was prepared as follows. Total RNA was extracted from 400 milliliters (mL) of buffy coat prepared from approximately 1 liter of fresh horse blood, using the acid-guanidinium-phenol-chloroform method generally described in Chomzynski et al., 1987, *Anal. Biochem.*, vol. 162, pp. 156–159. Poly $A^+$ RNA was isolated from the total RNA preparation using the mRNA Purification Kit (available from Pharmacia Biotech, Newark, N.J.), according to the method recommended by the manufacturer. The horse buffy coat cDNA library was constructed in lambda-Uni-ZAP™XR vector (available from Stratagene, La Jolla, Calif.), using Stratagene's ZAP-cDNA Synthesis Kit protocol. Approximately 5 milligrams (mg) of Poly $A^+$ RNA was used to produce the horse buffy coat cDNA library.

The horse buffy coat cDNA library was screened, using duplicate plaque filter lifts, with a $^{32}$P-labeled cDNA encoding the human $Fc_{\epsilon}R\alpha$ chain under the following conditions. The filters were pre-hybridized and hybridized in a hybridization solution including 5×SSC, 5×Denhardts, 0.5% SDS and $10^{\circ}$ $\mu$g/ml salmon sperm DNA. The filters were then washed in a wash buffer including 0.2×SSC and 0.1% SDS at about 55° C. A plaque identified in the screen was purified and converted into a double stranded recombinant molecule, herein denoted as $neqFc_{\epsilon}R\alpha_{1015}$, using the ExAssist™ helper phage and SOLR™ *E. coli* according to the in vivo excision protocol described in the ZAP-cDNA Synthesis Kit. Double-stranded plasmid DNA was prepared using an alkaline lysis protocol, such as that described in Sambrook et al., ibid.

Example 2

This example describes the sequencing of an equine $Fc_{\epsilon}R\alpha$ chain nucleic acid molecule of the present invention.

A plasmid containing neqFc$_\epsilon$Rα$_{1015}$ was sequenced by the Sanger dideoxy chain termination method, using the PRISM™ Ready Dye Terminator Cycle Sequencing Kit with Ampli Taq DNA Polymerase, FS (available from the Perkin-Elmer Corporation, Norwalk, Conn.). PCR extensions were done in the GeneAmp™ PCR System 9600 (available from Perkin-Elmer). Excess dye terminators were removed from extension products using the Centriflex™ Gel Filtration Cartridge (available from Advanced Genetics Technologies Corporation, Gaithersburg, Md.) following the standard protocol provided by the manufacturer. Samples were resuspended according to ABI protocols and were run on a Perkin-Elmer ABI PRISM™ 377 Automated DNA Sequencer. DNA sequence analysis, including the compilation of sequences and the determination of open reading frames, were performed using the GCG™ program (available from Genetics Computer Group, Madison, Wis.). Protein sequence analysis, including the determination of molecular weight and isoelectric point (pI) was performed using the GCG™ program.

An about 1015 nucleotide consensus sequence of the entire neqFc™ Rα$_{1015}$ DNA fragment was determined; the sequences of the two complementary strands are presented as SEQ ID NO:1 (the coding strand) and SEQ ID NO:3 (the complementary strand). The equine neqFc$_\epsilon$Rα$_{1015}$ sequence contains an apparent full length coding region. The apparent initiation codon spans from nucleotide 12 to nucleotide 14 and the apparent termination codon spans from nucleotide 777 to nucleotide 779, respectively, of SEQ ID NO:1. A putative polyadenylation signal (5' AATAAA 3') is located in a region spanning from nucleotide 976–981 of SEQ ID NO:1.

Translation of SEQ ID NO:1 yields a protein of about 255 amino acids, denoted PequFc$_\epsilon$Rα$_{255}$, the amino acid sequence of which is presented in SEQ ID NO:2. The nucleic acid molecule consisting of the coding region encoding PequFc$_\epsilon$Rα$_{255}$ is referred to herein as neqFc$_\epsilon$Rα$_{765}$, the nucleic acid sequence of which is represented in SEQ ID NO:4 (the coding strand) and SEQ ID NO:5 (the complementary strand). The amino acid sequence of PequFc$_\epsilon$Rα$_{255}$ (i.e., SEQ ID NO:2) predicts that PequFc$_\epsilon$Rα$_{255}$ has an estimated molecular weight of about 29.4 kD and an estimated pI of about 9.77. Analysis of SEQ ID NO:2 suggests the presence of a signal peptide spanning from amino acid 1 through amino acid 19. The proposed mature protein, denoted herein as PequFc$_\epsilon$Rα$_{236}$, contains about 236 amino acids which is represented herein as SEQ ID NO:7. PequFc$_\epsilon$Rα$_{236}$ is encoded by neqFc$_\epsilon$Rα$_{708}$ having a nucleic acid sequence represented herein as SEQ ID NO:6 and a complement represented herein as SEQ ID NO:8. The amino acid sequence of PequFc$_\epsilon$Rα$_{236}$ (i.e., SEQ ID NO:7) predicts that PequFc$_\epsilon$Rα$_{236}$ has an estimated molecular weight of about 27.3 kD, an estimated pI of about 9.77 and seven predicted asparagine-linked glycosylation sites extending from amino acids 46–48, 60–62, 67–69, 79–81, 99–101, 160–162, and 195–197 respectively.

Homology searches of the non-redundant protein and nucleotide sequence databases were performed through the National Center for Biotechnology Information using the BLAST network. The protein database includes SwissProt+ PIR+SPUpdate+Genpept+GPUpdate. The nucleotide database includes GenBank+EMBL+DDBJ+PDB. The highest scoring match of the homology search at the amino acid level was SwissProt accession number P12319: human high affinity IgE receptor α-chain, which was about 61% identical with SEQ ID NO:2. At the nucleotide level, the search was performed using SEQ ID NO:1, which was most similar to GenBank accession number X06948, human mRNA for immunoglobulin E receptor alpha chain, which was about 75% identical to SEQ ID NO:1.

Example 3

This Example demonstrates the production of an equine Fc$_\epsilon$Rα chain protein in eukaryotic cells.

Recombinant molecule pFB-neqFc$_\epsilon$Rα$_{603}$, containing an equine neqFc$_\epsilon$Rα nucleic acid molecule spanning nucleotides from 12 through 614 of SEQ ID NO:1, operatively linked to baculovirus polyhedron transcription control sequences, was produced in the following manner. An equine Fc$_\epsilon$Rα nucleic acid molecule-containing fragment of about 603 nucleotides was PCR amplified from neqFc$_\epsilon$Rα$_{1015}$ using sense primer EqIgErFor having the nucleic acid sequence 5' GCG GGA TCC TAT AAA TAT GCC TGC TCC CAT GGG 3' (SEQ ID NO:9; BamHI site shown in bold) and antisense primer EqIgERRev having the nucleic acid sequence 5' GCG CTG CAG TTA AGC TTT TTT TAC AGT AAT GTT GAG 3' (SEQ ID NO:10; PstI site shown in bold). The N-terminal primer was designed from the pol h sequence of baculovirus with modifications to enhance expression in the baculovirus system.

The resulting PCR product, which represents the coding region of neqFc$_\epsilon$Rα$_{1015}$, referred to as Bv-neqFc$_\epsilon$Rα$_{603}$ (herein designated SEQ ID NO:11) was digested with BamHI and PstI and subcloned into the unique BamHI and PstI sites of pFASTBAC1 baculovirus shuttle plasmid (available from Pharmingen, San Diego, Calif.) to produce the recombinant molecule referred to herein as pFB-neqFc$_\epsilon$Rα$_{603}$. Translation of SEQ ID NO:11 indicates that the nucleic acid molecule neqFc$_\epsilon$Rα$_{603}$ encodes a Fc$_\epsilon$Rα protein of about 201 amino acids, referred to herein as PequFc$_\epsilon$Rα$_{201}$, having amino acid sequence SEQ ID NO:12.

The resultant recombinant molecule, pFB-neqFc$_\epsilon$Rα$_{603}$, was verified for proper insert orientation by restriction mapping. Such a recombinant molecule can be co-transfected with a linear Baculogold baculovirus DNA (available from Pharmingen) into *S. frugiperda* Sf9 cells (available from InVitrogen, Carlsbad, Calif.) to form the recombinant cell denoted *S. frugiperda* pFB-neqFc$_\epsilon$RI(α)$_{603}$. *S. frugiperda*: pFB-neqFc$_\epsilon$Rα$_{603}$ can be cultured using conditions known to those skilled in the art in order to produce the equine Fc$_\epsilon$Rα protein, PequFc$_\epsilon$Rα$_{201}$ or a secreted form thereof.

What is claimed is:

1. A composition comprising an excipient and an isolated equine Fc$_\epsilon$R$\alpha$ protein comprising an amino acid sequence selected from the group consisting of SEQ ID NO:2, SEQ ID NO:7, SEQ ID NO:12 and amino acid sequences at least 95% identical to an amino acid sequence selected from the group consisting of SEQ ID NO:2, SEQ ID NO:7, and SEQ ID NO:12, wherein said protein comprises an IgE binding domain and binds to IgE.

2. The composition of claim 1, wherein said equine Fc$_\epsilon$R$\alpha$ protein is a soluble equine Fc$_\epsilon$R$\alpha$ protein that binds to IgE.

3. The composition of claim 1, wherein said composition further comprises a carrier.

4. The composition of claim 1, wherein said isolated equine Fc$_\epsilon$R$\alpha$ protein is encoded by a nucleic acid molecule comprising a nucleic acid sequence selected from the group consisting of: SEQ ID NO:1, SEQ ID NO:4, SEQ ID NO:6 and SEQ ID NO:11.

5. The composition of claim 1, wherein said isolated equine Fc$_\epsilon$R$\alpha$ protein comprises an amino acid sequence selected from the group consisting of SEQ ID NO:2, SEQ ID NO:7, and SEQ ID NO:12.

6. An isolated equine Fc$_\epsilon$R$\alpha$ protein comprising an amino acid sequence selected from the group consisting of SEQ ID NO:2, SEQ ID NO:7, and SEQ ID NO:12.

7. An isolated equine Fc$_\epsilon$R$\alpha$ protein comprising an amino acid sequence selected from the group consisting of SEQ ID NO:2, SEQ ID NO:7, SEQ ID NO:12 and amino acid sequences at least 95% identical to an amino acid sequence selected from the group consisting of SEQ ID NO:2, SEQ ID NO:7, and SEQ ID NO:12, wherein said protein comprises an IgE binding domain and binds to IgE.

8. The protein of claim 7, wherein said protein is encoded by a nucleic acid molecule comprising a nucleic acid sequence selected from the group consisting of: SEQ ID NO:1, SEQ ID NO:4, SEQ ID NO:6, and SEQ ID NO:11.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 1015 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 12..776

(xi) SEQUENCE DESCRIPTION: SEQ ID NO:1:

```
CCACAGAGGA G ATG CCT GCT CCC ATG GGA AGC CCT GCC CTG CTG              44
             Met Pro Ala Pro Met Gly Ser Pro Ala Leu Leu
               1               5                  10

TGG ATA ACT TTT CTG CTC TTC TCT CTG GAT GGC GTG CCA GCA               86
Trp Ile Thr Phe Leu Leu Phe Ser Leu Asp Gly Val Pro Ala
 15                  20                  25

GCC ATC CGG AAA TCT ACA GTG TCC TTG AAT CCC CCA TGG AAT              128
Ala Ile Arg Lys Ser Thr Val Ser Leu Asn Pro Pro Trp Asn
 30                  35

AGA ATA TTT CGA GGA GAG AAT GTG ACT CTT ACA TGT AAT AAG              170
Arg Ile Phe Arg Gly Glu Asn Val Thr Leu Thr Cys Asn Lys
 40                  45                      50

AAC AAG CCC CTT AAA GGC AAC TCC ACT GAG TGG ACC TAC AAC              212
Asn Lys Pro Leu Lys Gly Asn Ser Thr Glu Trp Thr Tyr Asn
 55                  60                      65

AAC ACC ACT TTA GAA GTG ACA ACT TCA AGT TTG AAC ATC ACT              254
Asn Thr Thr Leu Glu Val Thr Thr Ser Ser Leu Asn Ile Thr
 70                  75                      80

AAT GCC TCA CAC CGG AGC AGT GGG GAA TAC AGA TGT CGG AAC              296
Asn Ala Ser His Arg Ser Ser Gly Glu Tyr Arg Cys Arg Asn
 85                  90                      95

AAT GAC TTG AAC CTG AGT GAA GCT GTG CAC CTA GAA GTT TTC              338
Asn Asp Leu Asn Leu Ser Glu Ala Val His Leu Glu Val Phe
100                 105

AGT GAC TGG CTG CTC CTT CAG GCC TCT GCT GAG GAG GTC ATA              380
Ser Asp Trp Leu Leu Leu Gln Ala Ser Ala Glu Glu Val Ile
110                 115                 120

GAG GGT AAG GCC CTC GTT CTC AGG TGC CGT GGC TGG AAG GAT              422
Glu Gly Lys Ala Leu Val Leu Arg Cys Arg Gly Trp Lys Asp
125                 130                 135

TGG GAC GTC TTC AAG GTG ATC TAC TAC AAG GAT GGC AAA CCC              464
Trp Asp Val Phe Lys Val Ile Tyr Tyr Lys Asp Gly Lys Pro
140                 145                 150

CTC GAG TAC TGG TAT GAG AAC AAA AAC ATC TCC ATT GAA AGT              506
Leu Glu Tyr Trp Tyr Glu Asn Lys Asn Ile Ser Ile Glu Ser
155                 160                 165

GCC ACA ACA GAA AAC AGT GGC ACC TAT TAC TGC GAG GGT GCT              548
Ala Thr Thr Glu Asn Ser Gly Thr Tyr Tyr Cys Glu Gly Ala
170                 175

TTT AAC TTT AAG CGA ACA AGT GAA CGC TAT ACC TCT GAT TAC              590
Phe Asn Phe Lys Arg Thr Ser Glu Arg Tyr Thr Ser Asp Tyr
180                 185                 190

CTC AAC ATT ACT GTA AAA AAA GCT GAG CAA AGC AAA CGC TAC              632
Leu Asn Ile Thr Val Lys Lys Ala Glu Gln Ser Lys Arg Tyr
195                 200                 205

TGG CTA CAA TTT ATT ATT CCA TTG TTG GTG GTG ATT CTG TTT              674
Trp Leu Gln Phe Ile Ile Pro Leu Leu Val Val Ile Leu Phe
```

```
                    210                 215                 220
GCT GTG GAC ACA GGA TTG TTT GTC TCG ACC CAG CAG CAG TTA                716
Ala Val Asp Thr Gly Leu Phe Val Ser Thr Gln Gln Gln Leu
225                 230                 235

ACA TTT CTC TTG AAG ATT AAG AGG ACC AGG AGA GGC AGA AAA                758
Thr Phe Leu Leu Lys Ile Lys Arg Thr Arg Arg Gly Arg Lys
240                 245

CTT ATG GAC CCC CAT CCT TAAGTGAGAC CCGAGAAAGA ACTGATGTCA               806
Leu Met Asp Pro His Pro
250                 255

CTGCTCAAGA AACCTTTGCA ACAGCAATTT CTTCCTGGCA TCAGCAATTG                 856

CTTTTCAGTT GTCAAACACA GATCATAATG TACATAGAAA GGTCTATGCC                 906

CACGGCTTTG CAGAATTGCA TCATTAAACT AACTAGAACT GGTTAAGTGG                 956

CATGTAATAG TAAGTGCTCA ATAAACATCA TTTAAATAAA TATAAAAAAA                1006

AAAAAAAA                                                              1015

(2) INFORMATION FOR SEQ ID NO:2:

(i) SEQUENCE CHARACTERISTICS:
        (A) LENGTH: 255 amino acids
        (B) TYPE: amino acid
        (D) TOPOLOGY: linear (ii) MOLECULE TYPE: Protein (xi) SEQUENCE DESCRIPTION: SEQ ID NO:2:

Met Pro Ala Pro Met Gly Ser Pro Ala Leu Leu Trp Ile Thr
1               5                   10

Phe Leu Leu Phe Ser Leu Asp Gly Val Pro Ala Ala Ile Arg
15                  20                  25

Lys Ser Thr Val Ser Leu Asn Pro Pro Trp Asn Arg Ile Phe
30                  35                  40

Arg Gly Glu Asn Val Thr Leu Thr Cys Asn Lys Asn Lys Pro
45                  50                  55

Leu Lys Gly Asn Ser Thr Glu Trp Thr Tyr Asn Asn Thr Thr
60                  65                  70

Leu Glu Val Thr Thr Ser Ser Leu Asn Ile Thr Asn Ala Ser
75                  80

His Arg Ser Ser Gly Glu Tyr Arg Cys Arg Asn Asn Asp Leu
85                  90                  95

Asn Leu Ser Glu Ala Val His Leu Glu Val Phe Ser Asp Trp
100                 105                 110

Leu Leu Leu Gln Ala Ser Ala Glu Glu Val Ile Glu Gly Lys
115                 120                 125

Ala Leu Val Leu Arg Cys Arg Gly Trp Lys Asp Trp Asp Val
130                 135                 140

Phe Lys Val Ile Tyr Tyr Lys Asp Gly Lys Pro Leu Glu Tyr
145                 150

Trp Tyr Glu Asn Lys Asn Ile Ser Ile Glu Ser Ala Thr Thr
155                 160                 165

Glu Asn Ser Gly Thr Tyr Tyr Cys Glu Gly Ala Phe Asn Phe
170                 175                 180

Lys Arg Thr Ser Glu Arg Tyr Thr Ser Asp Tyr Leu Asn Ile
185                 190                 195

Thr Val Lys Lys Ala Glu Gln Ser Lys Arg Tyr Trp Leu Gln
```

```
200                205                210
Phe Ile Ile Pro Leu Leu Val Val Ile Leu Phe Ala Val Asp
215                220

Thr Gly Leu Phe Val Ser Thr Gln Gln Gln Leu Thr Phe Leu
225                230                235

Leu Lys Ile Lys Arg Thr Arg Arg Gly Arg Lys Leu Met Asp
240                245                250

Pro His Pro
255
```

(2) INFORMATION FOR SEQ ID NO:3:

(i) SEQUENCE CHARACTERISTICS:
        (A) LENGTH: 1015 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:3:

```
TTTTTTTTTT TTTTTTATAT TTATTTAAAT GATGTTTATT GAGCACTTAC         50
TATTACATGC CACTTAACCA GTTCTAGTTA GTTTAATGAT GCAATTCTGC        100
AAAGCCGTGG GCATAGACCT TTCTATGTAC ATTATGATCT GTGTTTGACA        150
ACTGAAAAGC AATTGCTGAT GCCAGGAAGA AATTGCTGTT GCAAAGGTTT        200
CTTGAGCAGT GACATCAGTT CTTTCTCGGG TCTCACTTAA GGATGGGGGT        250
CCATAAGTTT TCTGCCTCTC CTGGTCCTCT TAATCTTCAA GAGAAATGTT        300
AACTGCTGCT GGGTCGAGAC AAACAATCCT GTGTCCACAG CAAACAGAAT        350
CACCACCAAC AATGGAATAA TAAATTGTAG CCAGTAGCGT TTGCTTTGCT        400
CAGCTTTTTT TACAGTAATG TTGAGGTAAT CAGAGGTATA GCGTTCACTT        450
GTTCGCTTAA AGTTAAAAGC ACCCTCGCAG TAATAGGTGC CACTGTTTTC        500
TGTTGTGGCA CTTTCAATGG AGATGTTTTT GTTCTCATAC CAGTACTCGA        550
GGGGTTTGCC ATCCTTGTAG TAGATCACCT TGAAGACGTC CCAATCCTTC        600
CAGCCACGGC ACCTGAGAAC GAGGGCCTTA CCCTCTATGA CCTCCTCAGC        650
AGAGGCCTGA AGGAGCAGCC AGTCACTGAA AACTTCTAGG TGCACAGCTT        700
CACTCAGGTT CAAGTCATTG TTCCGACATC TGTATTCCCC ACTGCTCCGG        750
TGTGAGGCAT TAGTGATGTT CAAACTTGAA GTTGTCACTT CTAAAGTGGT        800
GTTGTTGTAG GTCCACTCAG TGGAGTTGCC TTTAAGGGGC TTGTTCTTAT        850
TACATGTAAG AGTCACATTC TCTCCTCGAA ATATTCTATT CCATGGGGGA        900
TTCAAGGACA CTGTAGATTT CCGGATGGCT GCTGGCACGC CATCCAGAGA        950
GAAGAGCAGA AAAGTTATCC ACAGCAGGGC AGGGCTTCCC ATGGGAGCAG       1000
GCATCTCCTC TGTGG                                             1015
```

(2) INFORMATION FOR SEQ ID NO:4:

(i) SEQUENCE CHARACTERISTICS:
        (A) LENGTH: 765 nucleotides
        (B) TYPE: nucleic acid
        (C) STRANDEDNESS: single
        (D) TOPOLOGY: linear (ii) MOLECULE TYPE: cDNA

```
    (ix) FEATURE:
         (A) NAME/KEY: CDS
         (B) LOCATION: 1..765

(xi) SEQUENCE DESCRIPTION: SEQ ID NO:4:

ATG CCT GCT CCC ATG GGA AGC CCT GCC CTG CTG TGG ATA ACT            42
Met Pro Ala Pro Met Gly Ser Pro Ala Leu Leu Trp Ile Thr
1               5                   10

TTT CTG CTC TTC TCT CTG GAT GGC GTG CCA GCA GCC ATC CGG            84
Phe Leu Leu Phe Ser Leu Asp Gly Val Pro Ala Ala Ile Arg
15                  20                  25

AAA TCT ACA GTG TCC TTG AAT CCC CCA TGG AAT AGA ATA TTT           126
Lys Ser Thr Val Ser Leu Asn Pro Pro Trp Asn Arg Ile Phe
30                  35                  40

CGA GGA GAG AAT GTG ACT CTT ACA TGT AAT AAG AAC AAG CCC           168
Arg Gly Glu Asn Val Thr Leu Thr Cys Asn Lys Asn Lys Pro
45                  50                  55

CTT AAA GGC AAC TCC ACT GAG TGG ACC TAC AAC AAC ACC ACT           210
Leu Lys Gly Asn Ser Thr Glu Trp Thr Tyr Asn Asn Thr Thr
60                  65                  70

TTA GAA GTG ACA ACT TCA AGT TTG AAC ATC ACT AAT GCC TCA           252
Leu Glu Val Thr Thr Ser Ser Leu Asn Ile Thr Asn Ala Ser
75                  80

CAC CGG AGC AGT GGG GAA TAC AGA TGT CGG AAC AAT GAC TTG           294
His Arg Ser Ser Gly Glu Tyr Arg Cys Arg Asn Asn Asp Leu
85                  90                  95

AAC CTG AGT GAA GCT GTG CAC CTA GAA GTT TTC AGT GAC TGG           336
Asn Leu Ser Glu Ala Val His Leu Glu Val Phe Ser Asp Trp
100                 105                 110

CTG CTC CTT CAG GCC TCT GCT GAG GAG GTC ATA GAG GGT AAG           378
Leu Leu Leu Gln Ala Ser Ala Glu Glu Val Ile Glu Gly Lys
115                 120                 125

GCC CTC GTT CTC AGG TGC CGT GGC TGG AAG GAT TGG GAC GTC           420
Ala Leu Val Leu Arg Cys Arg Gly Trp Lys Asp Trp Asp Val
130                 135                 140

TTC AAG GTG ATC TAC TAC AAG GAT GGC AAA CCC CTC GAG TAC           462
Phe Lys Val Ile Tyr Tyr Lys Asp Gly Lys Pro Leu Glu Tyr
145                 150

TGG TAT GAG AAC AAA AAC ATC TCC ATT GAA AGT GCC ACA ACA           504
Trp Tyr Glu Asn Lys Asn Ile Ser Ile Glu Ser Ala Thr Thr
155                 160                 165

GAA AAC AGT GGC ACC TAT TAC TGC GAG GGT GCT TTT AAC TTT           546
Glu Asn Ser Gly Thr Tyr Tyr Cys Glu Gly Ala Phe Asn Phe
170                 175                 180

AAG CGA ACA AGT GAA CGC TAT ACC TCT GAT TAC CTC AAC ATT           588
Lys Arg Thr Ser Glu Arg Tyr Thr Ser Asp Tyr Leu Asn Ile
185                 190                 195

ACT GTA AAA AAA GCT GAG CAA AGC AAA CGC TAC TGG CTA CAA           630
Thr Val Lys Lys Ala Glu Gln Ser Lys Arg Tyr Trp Leu Gln
200                 205                 210

TTT ATT ATT CCA TTG TTG GTG GTG ATT CTG TTT GCT GTG GAC           672
Phe Ile Ile Pro Leu Leu Val Val Ile Leu Phe Ala Val Asp
215                 220

ACA GGA TTG TTT GTC TCG ACC CAG CAG CAG TTA ACA TTT CTC           714
Thr Gly Leu Phe Val Ser Thr Gln Gln Gln Leu Thr Phe Leu
225                 230                 235

TTG AAG ATT AAG AGG ACC AGG AGA GGC AGA AAA CTT ATG GAC           756
Leu Lys Ile Lys Arg Thr Arg Arg Gly Arg Lys Leu Met Asp
240                 245                 250
```

```
CCC CAT CCT                                                                    765
Pro His Pro
255

(2) INFORMATION FOR SEQ ID NO:5:

(i) SEQUENCE CHARACTERISTICS:
        (A) LENGTH:  765 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:5:

AGGATGGGGG TCCATAAGTT TTCTGCCTCT CCTGGTCCTC TTAATCTTCA           50

AGAGAAATGT TAACTGCTGC TGGGTCGAGA CAAACAATCC TGTGTCCACA          100

GCAAACAGAA TCACCACCAA CAATGGAATA ATAAATTGTA GCCAGTAGCG          150

TTTGCTTTGC TCAGCTTTTT TTACAGTAAT GTTGAGGTAA TCAGAGGTAT          200

AGCGTTCACT TGTTCGCTTA AAGTTAAAAG CACCCTCGCA GTAATAGGTG          250

CCACTGTTTT CTGTTGTGGC ACTTTCAATG GAGATGTTTT TGTTCTCATA          300

CCAGTACTCG AGGGGTTTGC CATCCTTGTA GTAGATCACC TTGAAGACGT          350

CCCAATCCTT CCAGCCACGG CACCTGAGAA CGAGGGCCTT ACCCTCTATG          400

ACCTCCTCAG CAGAGGCCTG AAGgAGCAGC CAGTCACTGA AAACTTCTAG          450

GTGCACAGCT TCACTCAGGT TCAAGTCATT GTTCCGACAT CTGTATTCCC          500

CACTGCTCCG GTGTGAGGCA TTAGTGATGT TCAAACTTGA AGTTGTCACT          550

TCTAAAGTGG TGTTGTTGTA GGTCCACTCA GTGGAGTTGC CTTTAAGGGG          600

CTTGTTCTTA TTACATGTAA GAGTCACATT CTCTCCTCGA AATATTCTAT          650

TCCATGGGGG ATTCAAGGAC ACTGTAGATT TCCGGATGGC TGCTGGCACG          700

CCATCCAGAG AGAAGAGCAG AAAAGTTATC CACAGCAGGG CAGGGCTTCC          750

CATGGGAGCA GGCAT                                                765

(2) INFORMATION FOR SEQ ID NO:6:

(i) SEQUENCE CHARACTERISTICS:
        (A) LENGTH:  708 nucleotides
        (B) TYPE:  nucleic acid
        (C) STRANDEDNESS:  single
        (D) TOPOLOGY:  linear (ii) MOLECULE TYPE:  cDNA (ix) FEATURE:
        (A) NAME/KEY:  CDS
        (B) LOCATION:  1..708

(xi) SEQUENCE DESCRIPTION:  SEQ ID NO:6:

CTG GAT GGC GTG CCA GCA GCC ATC CGG AAA TCT ACA GTG TCC           42
Leu Asp Gly Val Pro Ala Ala Ile Arg Lys Ser Thr Val Ser
1               5                  10

TTG AAT CCC CCA TGG AAT AGA ATA TTT CGA GGA GAG AAT GTG           84
Leu Asn Pro Pro Trp Asn Arg Ile Phe Arg Gly Glu Asn Val
15                  20                  25

ACT CTT ACA TGT AAT AAG AAC AAG CCC CTT AAA GGC AAC TCC          126
Thr Leu Thr Cys Asn Lys Asn Lys Pro Leu Lys Gly Asn Ser
30                  35                  40

ACT GAG TGG ACC TAC AAC AAC ACC ACT TTA GAA GTG ACA ACT          168
Thr Glu Trp Thr Tyr Asn Asn Thr Thr Leu Glu Val Thr Thr
```

```
                 45              50              55
TCA AGT TTG AAC ATC ACT AAT GCC TCA CAC CGG AGC AGT GGG                210
Ser Ser Leu Asn Ile Thr Asn Ala Ser His Arg Ser Ser Gly
60              65              70

GAA TAC AGA TGT CGG AAC AAT GAC TTG AAC CTG AGT GAA GCT                252
Glu Tyr Arg Cys Arg Asn Asn Asp Leu Asn Leu Ser Glu Ala
75              80

GTG CAC CTA GAA GTT TTC AGT GAC TGG CTG CTC CTT CAG GCC                294
Val His Leu Glu Val Phe Ser Asp Trp Leu Leu Leu Gln Ala
85              90              95

TCT GCT GAG GAG GTC ATA GAG GGT AAG GCC CTC GTT CTC AGG                336
Ser Ala Glu Glu Val Ile Glu Gly Lys Ala Leu Val Leu Arg
100             105             110

TGC CGT GGC TGG AAG GAT TGG GAC GTC TTC AAG GTG ATC TAC                378
Cys Arg Gly Trp Lys Asp Trp Asp Val Phe Lys Val Ile Tyr
115             120             125

TAC AAG GAT GGC AAA CCC CTC GAG TAC TGG TAT GAG AAC AAA                420
Tyr Lys Asp Gly Lys Pro Leu Glu Tyr Trp Tyr Glu Asn Lys
130             135             140

AAC ATC TCC ATT GAA AGT GCC ACA ACA GAA AAC AGT GGC ACC                462
Asn Ile Ser Ile Glu Ser Ala Thr Thr Glu Asn Ser Gly Thr
145             150

TAT TAC TGC GAG GGT GCT TTT AAC TTT AAG CGA ACA AGT GAA                504
Tyr Tyr Cys Glu Gly Ala Phe Asn Phe Lys Arg Thr Ser Glu
155             160             165

CGC TAT ACC TCT GAT TAC CTC AAC ATT ACT GTA AAA AAA GCT                546
Arg Tyr Thr Ser Asp Tyr Leu Asn Ile Thr Val Lys Lys Ala
170             175             180

GAG CAA AGC AAA CGC TAC TGG CTA CAA TTT ATT ATT CCA TTG                588
Glu Gln Ser Lys Arg Tyr Trp Leu Gln Phe Ile Ile Pro Leu
185             190             195

TTG GTG GTG ATT CTG TTT GCT GTG GAC ACA GGA TTG TTT GTC                630
Leu Val Val Ile Leu Phe Ala Val Asp Thr Gly Leu Phe Val
200             205             210

TCG ACC CAG CAG CAG TTA ACA TTT CTC TTG AAG ATT AAG AGG                672
Ser Thr Gln Gln Gln Leu Thr Phe Leu Leu Lys Ile Lys Arg
215             220

ACC AGG AGA GGC AGA AAA CTT ATG GAC CCC CAT CCT                        708
Thr Arg Arg Gly Arg Lys Leu Met Asp Pro His Pro
225             230             235

(2) INFORMATION FOR SEQ ID NO:7:

(i) SEQUENCE CHARACTERISTICS:
        (A) LENGTH:   236 amino acids
        (B) TYPE:     amino acid
        (D) TOPOLOGY: linear (ii) MOLECULE TYPE: Protein (xi) SEQUENCE DESCRIPTION: SEQ ID NO:7:

Leu Asp Gly Val Pro Ala Ala Ile Arg Lys Ser Thr Val Ser
1               5               10

Leu Asn Pro Pro Trp Asn Arg Ile Phe Arg Gly Glu Asn Val
15              20              25

Thr Leu Thr Cys Asn Lys Asn Lys Pro Leu Lys Gly Asn Ser
30              35              40

Thr Glu Trp Thr Tyr Asn Asn Thr Thr Leu Glu Val Thr Thr
45              50              55

Ser Ser Leu Asn Ile Thr Asn Ala Ser His Arg Ser Ser Gly
```

```
 60              65              70
Glu Tyr Arg Cys Arg Asn Asn Asp Leu Asn Leu Ser Glu Ala
75                  80

Val His Leu Glu Val Phe Ser Asp Trp Leu Leu Leu Gln Ala
85                  90                  95

Ser Ala Glu Glu Val Ile Glu Gly Lys Ala Leu Val Leu Arg
100                 105                 110

Cys Arg Gly Trp Lys Asp Trp Asp Val Phe Lys Val Ile Tyr
115                 120                 125

Tyr Lys Asp Gly Lys Pro Leu Glu Tyr Trp Tyr Glu Asn Lys
130                 135                 140

Asn Ile Ser Ile Glu Ser Ala Thr Thr Glu Asn Ser Gly Thr
145                 150

Tyr Tyr Cys Glu Gly Ala Phe Asn Phe Lys Arg Thr Ser Glu
155                 160                 165

Arg Tyr Thr Ser Asp Tyr Leu Asn Ile Thr Val Lys Lys Ala
170                 175                 180

Glu Gln Ser Lys Arg Tyr Trp Leu Gln Phe Ile Ile Pro Leu
185                 190                 195

Leu Val Val Ile Leu Phe Ala Val Asp Thr Gly Leu Phe Val
200                 205                 210

Ser Thr Gln Gln Gln Leu Thr Phe Leu Leu Lys Ile Lys Arg
215                 220

Thr Arg Arg Gly Arg Lys Leu Met Asp Pro His Pro
225                 230                 235

(2) INFORMATION FOR SEQ ID NO:8:

(i) SEQUENCE CHARACTERISTICS:
        (A) LENGTH: 708 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

AGGATGGGGG TCCATAAGTT TTCTGCCTCT CCTGGTCCTC TTAATCTTCA         50

AGAGAAATGT TAACTGCTGC TGGGTCGAGA CAAACAATCC TGTGTCCACA        100

GCAAACAGAA TCACCACCAA CAATGGAATA ATAAATTGTA GCCAGTAGCG        150

TTTGCTTTGC TCAGCTTTTT TTACAGTAAT GTTGAGGTAA TCAGAGGTAT        200

AGCGTTCACT TGTTCGCTTA AAGTTAAAAG CACCCTCGCA GTAATAGGTG        250

CCACTGTTTT CTGTTGTGGC ACTTTCAATG GAGATGTTTT TGTTCTCATA        300

CCAGTACTCG AGGGGTTTGC CATCCTTGTA GTAGATCACC TTGAAGACGT        350

CCCAATCCTT CCAGCCACGG CACCTGAGAA CGAGGGCCTT ACCCTCTATG        400

ACCTCCTCAG CAGAGGCCTG AAGgAGCAGC CAGTCACTGA AAACTTCTAG        450

GTGCACAGCT TCACTCAGGT TCAAGTCATT GTTCCGACAT CTGTATTCCC        500

CACTGCTCCG GTGTGAGGCA TTAGTGATGT TCAAACTTGA AGTTGTCACT        550

TCTAAAGTGG TGTTGTTGTA GGTCCACTCA GTGGAGTTGC CTTTAAGGGG        600

CTTGTTCTTA TTCATGTAA GAGTCACATT CTCTCCTCGA AATATTCTAT        650

TCCATGGGGG ATTCAAGGAC ACTGTAGATT TCCGGATGGC TGCTGGCACG        700
```

```
CCATCCAG                                                            708

(2) INFORMATION FOR SEQ ID NO:9:

(i) SEQUENCE CHARACTERISTICS:
        (A) LENGTH:  33 nucleotides
        (B) TYPE:  nucleic acid
        (C) STRANDEDNESS:  single
        (D) TOPOLOGY:  linear (ii) MOLECULE TYPE:  Primer (xi) SEQUENCE DESCRIPTION:  SEQ ID NO:9:

GCGGGATCCT ATAAATATGC CTGCTCCCAT GGG                                 33

(2) INFORMATION FOR SEQ ID NO:10:

(i) SEQUENCE CHARACTERISTICS:
        (A) LENGTH:  36 nucleotides
        (B) TYPE:  nucleic acid
        (C) STRANDEDNESS:  single
        (D) TOPOLOGY:  linear (ii) MOLECULE TYPE:  Primer (xi) SEQUENCE DESCRIPTION:  SEQ ID NO:10:

GCGCTGCAGT TAAGCTTTTT TTACAGTAAT GTTGAG                              36

(2) INFORMATION FOR SEQ ID NO:11:

(i) SEQUENCE CHARACTERISTICS:
        (A) LENGTH: 603 nucleotides
        (B) TYPE:  nucleic acid
        (C) STRANDEDNESS:  single
        (D) TOPOLOGY:  linear (ii) MOLECULE TYPE:  cDNA (ix) FEATURE:
        (A) NAME/KEY:  CDS
        (B) LOCATION:  1..603

(xi) SEQUENCE DESCRIPTION:  SEQ ID NO:11:
```

```
ATG CCT GCT CCC ATG GGA AGC CCT GCC CTG CTG TGG ATA ACT              42
Met Pro Ala Pro Met Gly Ser Pro Ala Leu Leu Trp Ile Thr
 1               5                  10

TTT CTG CTC TTC TCT CTG GAT GGC GTG CCA GCA GCC ATC CGG              84
Phe Leu Leu Phe Ser Leu Asp Gly Val Pro Ala Ala Ile Arg
 15                  20                  25

AAA TCT ACA GTG TCC TTG AAT CCC CCA TGG AAT AGA ATA TTT             126
Lys Ser Thr Val Ser Leu Asn Pro Pro Trp Asn Arg Ile Phe
 30                  35                  40

CGA GGA GAG AAT GTG ACT CTT ACA TGT AAT AAG AAC AAG CCC             168
Arg Gly Glu Asn Val Thr Leu Thr Cys Asn Lys Asn Lys Pro
 45                  50                  55

CTT AAA GGC AAC TCC ACT GAG TGG ACC TAC AAC AAC ACC ACT             210
Leu Lys Gly Asn Ser Thr Glu Trp Thr Tyr Asn Asn Thr Thr
 60                  65                  70

TTA GAA GTG ACA ACT TCA AGT TTG AAC ATC ACT AAT GCC TCA             252
Leu Glu Val Thr Thr Ser Ser Leu Asn Ile Thr Asn Ala Ser
 75                  80

CAC CGG AGC AGT GGG GAA TAC AGA TGT CGG AAC AAT GAC TTG             294
His Arg Ser Ser Gly Glu Tyr Arg Cys Arg Asn Asn Asp Leu
 85                  90                  95

AAC CTG AGT GAA GCT GTG CAC CTA GAA GTT TTC AGT GAC TGG             336
Asn Leu Ser Glu Ala Val His Leu Glu Val Phe Ser Asp Trp
```

```
                                                                                          -continued 100                     105                     110

CTG CTC CTT CAG GCC TCT GCT GAG GAG GTC ATA GAG GGT AAG              378
Leu Leu Leu Gln Ala Ser Ala Glu Glu Val Ile Glu Gly Lys
115                     120                     125

GCC CTC GTT CTC AGG TGC CGT GGC TGG AAG GAT TGG GAC GTC              420
Ala Leu Val Leu Arg Cys Arg Gly Trp Lys Asp Trp Asp Val
130                     135                     140

TTC AAG GTG ATC TAC TAC AAG GAT GGC AAA CCC CTC GAG TAC              462
Phe Lys Val Ile Tyr Tyr Lys Asp Gly Lys Pro Leu Glu Tyr
145                     150

TGG TAT GAG AAC AAA AAC ATC TCC ATT GAA AGT GCC ACA ACA              504
Trp Tyr Glu Asn Lys Asn Ile Ser Ile Glu Ser Ala Thr Thr
155                     160                     165

GAA AAC AGT GGC ACC TAT TAC TGC GAG GGT GCT TTT AAC TTT              546
Glu Asn Ser Gly Thr Tyr Tyr Cys Glu Gly Ala Phe Asn Phe
170                     175                     180

AAG CGA ACA AGT GAA CGC TAT ACC TCT GAT TAC CTC AAC ATT              588
Lys Arg Thr Ser Glu Arg Tyr Thr Ser Asp Tyr Leu Asn Ile
185                     190                     195

ACT GTA AAA AAA GCT                                                  603
Thr Val Lys Lys Ala
200

(2) INFORMATION FOR SEQ ID NO:12:

(i) SEQUENCE CHARACTERISTICS:
        (A) LENGTH: 201 amino acids
        (B) TYPE: amino acid
        (D) TOPOLOGY: linear (ii) MOLECULE TYPE: Protein (xi) SEQUENCE DESCRIPTION: SEQ ID NO:12:

Met Pro Ala Pro Met Gly Ser Pro Ala Leu Leu Trp Ile Thr
1                   5                       10

Phe Leu Leu Phe Ser Leu Asp Gly Val Pro Ala Ala Ile Arg
15                      20                      25

Lys Ser Thr Val Ser Leu Asn Pro Pro Trp Asn Arg Ile Phe
30                      35                      40

Arg Gly Glu Asn Val Thr Leu Thr Cys Asn Lys Asn Lys Pro
45                      50                      55

Leu Lys Gly Asn Ser Thr Glu Trp Thr Tyr Asn Asn Thr Thr
60                      65                      70

Leu Glu Val Thr Thr Ser Ser Leu Asn Ile Thr Asn Ala Ser
75                      80

His Arg Ser Ser Gly Glu Tyr Arg Cys Arg Asn Asn Asp Leu
85                      90                      95

Asn Leu Ser Glu Ala Val His Leu Glu Val Phe Ser Asp Trp
100                     105                     110

Leu Leu Leu Gln Ala Ser Ala Glu Glu Val Ile Glu Gly Lys
115                     120                     125

Ala Leu Val Leu Arg Cys Arg Gly Trp Lys Asp Trp Asp Val
130                     135                     140

Phe Lys Val Ile Tyr Tyr Lys Asp Gly Lys Pro Leu Glu Tyr
145                     150

Trp Tyr Glu Asn Lys Asn Ile Ser Ile Glu Ser Ala Thr Thr
155                     160                     165

Glu Asn Ser Gly Thr Tyr Tyr Cys Glu Gly Ala Phe Asn Phe
```

```
                          -continued
170                 175                 180
Lys Arg Thr Ser Glu Arg Tyr Thr Ser Asp Tyr Leu Asn Ile
185                 190                 195

Thr Val Lys Lys Ala
200
```